US011779040B2

(12) United States Patent
Lucey et al.

(10) Patent No.: US 11,779,040 B2
(45) Date of Patent: *Oct. 10, 2023

(54) PRODUCTION OF PROTEIN-POLYSACCHARIDE CONJUGATES

(71) Applicant: WISCONSIN ALUMNI RESEARCH FOUNDATION, Madison, WI (US)

(72) Inventors: John A. Lucey, Madison, WI (US); Dani Zhu, Madison, WI (US); Srinivasan Damodaran, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/941,100

(22) Filed: Jul. 28, 2020

(65) Prior Publication Data

US 2020/0352205 A1 Nov. 12, 2020

Related U.S. Application Data

(63) Continuation of application No. 12/407,543, filed on Mar. 19, 2009.

(Continued)

(51) Int. Cl.
*A23L 29/30* (2016.01)
*A23L 33/125* (2016.01)
(Continued)

(52) U.S. Cl.
CPC .............. *A23L 29/30* (2016.08); *A23C 21/08* (2013.01); *A23J 3/08* (2013.01); *A23L 2/66* (2013.01);
(Continued)

(58) Field of Classification Search
CPC .......... A23I 29/30; A23L 229/30; A23L 5/00; A23L 27/62; A23L 29/10; A23L 33/125; A61K 35/20; C07K 14/4717
(Continued)

(56) References Cited

U.S. PATENT DOCUMENTS 6,573,245 B1 6/2003 Marciani
7,148,034 B2 12/2006 Schlothauer

FOREIGN PATENT DOCUMENTS

EP 2025235 A1 2/2009
WO WO 1997/041897 11/1997
(Continued)

OTHER PUBLICATIONS

Heinze et al., Functional Polymers Based on Dextran, Advances in Polymer Science 205(1):199-291, (2006).*
(Continued)

*Primary Examiner* — Donald R Spamer
*Assistant Examiner* — Philip A Dubois
(74) *Attorney, Agent, or Firm* — Daniel A. Blasiole; DeWitt LLP

(57) ABSTRACT

The present invention provides novel compositions and methods for producing protein-polysaccharide conjugates in aqueous solutions. Also provided are methods for limiting the Maillard reaction to the very initial stage, the formation of the Schiff base. Provided are methods to obtain a simple product of Schiff base with white color, and compositions obtained using the methods of the present invention.

14 Claims, 12 Drawing Sheets

Related U.S. Application Data

(60) Provisional application No. 61/037,912, filed on Mar. 19, 2008.

(51) Int. Cl.

| | |
|---|---|
| A23L 5/00 | (2016.01) |
| A23C 21/08 | (2006.01) |
| A23J 3/08 | (2006.01) |
| A23L 2/66 | (2006.01) |
| C08B 37/02 | (2006.01) |
| C08H 1/00 | (2006.01) |
| A61K 35/20 | (2006.01) |
| A23L 27/00 | (2016.01) |
| A23L 29/10 | (2016.01) |
| A23L 27/60 | (2016.01) |
| C07K 14/47 | (2006.01) |

(52) U.S. Cl.
CPC .............. *A23L 5/00* (2016.08); *A23L 27/60* (2016.08); *A23L 27/84* (2016.08); *A23L 29/10* (2016.08); *A23L 33/125* (2016.08); *A61K 35/20* (2013.01); *C07K 14/4717* (2013.01); *C08B 37/0021* (2013.01); *C08H 1/00* (2013.01); *A23V 2002/00* (2013.01)

(58) Field of Classification Search
USPC .......................................................... 426/656
See application file for complete search history.

(56) References Cited

FOREIGN PATENT DOCUMENTS

| WO | WO 2000/18249 | 4/2000 |
|---|---|---|
| WO | WO 2006/090110 A1 | 8/2006 |

OTHER PUBLICATIONS

New Physiochemical and Functional Properties by the Gylcosylation of Whey Protein, Journal of Protein Chemistry, vol. 17, No. 5,1998 (NACKA).*
Jiang, Journal of Colloid and Interface Science 301 (2006) 98-106 (Jiang).*
Augustin et al., Rheology of whey protein-dextran conjugate films at the air/water interface, Food Hydrocolloids 21 (2007) 1072-1080.*
Kulmyrzaev et al., Influence of Sucrose on the Thermal Denaturation, Gelation, and Emulsion Stabilization of Whey Proteins, J. Agric. Food Chem. 2000, 48, 1593-1597.
Babiker, Effect of Polysaccharide Conjugation or Transglutaminase Treatment on the Allergenicity and Functional Properties of Soy Protein, J. Agric. Food Chem. 1998, 46, 866-871.
First Examiners Report for Australian Patent Application No. 2009225516, dated Jul. 6, 2013.
Benichou, A. et al., Formation and characterisation of amphiphilic conjugates of whey protein isolate (WPI)/ xanthan to improve surface activity, Food Hydrocolloids, 2007, 21, 379-391.
Akhtar, M. et al., "Emulsifying properties of whey protein-dextran conjugates at low pH and different salt concentrations", Colloids and Surfaces B: Biointerfaces, 2003, 31, 125-132.
First Official Letter of the European Patent Office for European Patent Application No. 09721275.7, dated Mar. 25, 2011.
Examination Report of the New Zealand Intellectual Property Office for New Zealand Patent Application No. 586677, dated Mar. 14, 2011.
Written Opinion from PCT/US2009/037660, dated Aug. 3, 2009.
Ames, "Control of the Maillard Reaction in Food Systems," *Trends Food Sci. Tech.*, 1:150-154(1990).
Beecher et al., "Factors Regulating Astringency of Whey Protein Beverages," *J. Dairy Sci.*, 91:2553-2560 (2008).
Bionski et al., "Inhibition of Rabbit Muscle Aldolase by Phosphorylated Aromatic Compounds," *Biochem. J.*, 323:71-77 (1997).
Cadwallader et al., "A Note on Particulate Matter Encountered in Some Dextran Injuctions," *J. Amer. Pharm. Assoc.*, 47:894-895 (1958).
Cayot et al., "Electrochemical Modifications of Proteins. 1. Glycitolation," J. Agric. Food Chem., 47:1915-1923 (1999).
Chevalier et al., "Improvement of Function Properties of β-Lactoglobulin Glycated Through the Maillard Reaction is Related to the nature of the Sugar," *Int. Dairy J.*, 11:145-152 (2001).
Dickinson and Semenova, "Emulsifying Properties of Covalent Protein-Dextran Hybrids," *Colloids Surf.*, 64:299-310 (1992).
Dickinson, "Properties of Emulsions Stabilized with Milk Proteins: Overview of Some Recent Developments," *J. Dairy Sci.*, 80:2607-2619 (1997).
Dickinson and Galazka, "Emulsion Stabilization by Ionic and Covalent Complexes of β-lactoglobulin with *Polysaccharides,*" *Food Hydrocoll.*, 5:281-296 (1991).
Dunlap and Côté, "β-Lactoglobulin-Dextran Conjugates: Effect of Polysaccharide Size on Emulsion Stability," *J. Agric. Food Chem.*, 53:419-423 (2005).
Galazka et al., "Interactions of Ovalbumin with Sulphated Polysaccharides: Effects of pH Ionic Strength, Heat and High Pressure Treatment," *Food Hydrocoll.*, 13:81-88 (1999).
Garrett et al., "Thermal Denaturation and Coagulation of Whey Proteins: Effect of Sugars," *J. Dairy Sci.*, 71:10-16 (1998).
Hamilton and Adkinson, "Quantitation of Allergen-Specific IgE in Serum Using the Radioallergosorbent Test," *J. Clinical Immunoassay*, 6:147-153 (1983).
Hattori et al., "Reduced Immunogenicity of β-Lactoglobulin by Conjugation with Acidic Oligosaccharides," *J. Agricultural and Food Chemistry*, 52:4546-4553 (2004).
Heinert and Martell, "Pyridoxine and Pyridoxal Analogs. VI. Electronic Absorption Spectra of Schiff Bases," *J. Am. Chem. Soc.*, 85:183-188 (1963).
Hodge, "Chemistry of Browning Reactions in Model Systems," *J. Agric. Food Chem.*, 1:928-943(1953).
Hofmann, "Studies on the Relationship between Molecular Weight and the Color Potency of Fractions Obtained by Thermal Treatment of Glucose/Amino Acid and Glucose/Protein Solutions by Using Ultracentrifugation and Color Dilution Techniques," *J. Agric Food Chem.*, 46:3891-3895 (1998).
Horne et al., "Turbidity as a Measure of Salviary Protein Reactions with Astringent Substances," *Chem. Senses*, 27:653-659 (2002).
Isaacs and Coulson, "Effect of Pressure on Processes Modelling the Maillard Reaction," *J. Phys. Org. Chem.*, 9:639-644 (1996).
Laemmli, "Cleavage of Structural Proteins during the Assembly of the Head of Bacteriophage T4," *Nature*, 227:680-685 (1970).
López-Fandiño, "Functional Improvement of Milk Whey Proteins Induced by High Hydrostatic Pressure," *Crit. Rev. Food Sci. Nutr.*, 46:351-363 (2006).
Matheu et al., "Allergy to Lingonberry: A Case Report," *Clinical and Molecular Allergy*, 2:2 (2004).
McGuffey et al., "Denaturation and Aggregation of Three α-Lactalbumin Preparations at Neutral pH," *J. Agric. Food Chem.*, 53:3182-3190 (2005).
Minton, "Influence of Excluded vol. Upon Macromolecular Structure and Associations in 'Crowded' Media," *Curr. Opin. Biotech.*, 8:65-69 (1997).
Moreno et al., "High-Pressure Effects on Maillard Reaction between Glucose and Lysine," *J. Agric. Food Chem.*, 51:394-400 (2003).
Mulvihill and Donovan, "Whey Proteins and their Thermal Denaturation—A Review," *Irish J. Food Sci. Tech.*, 11:43-75 (1987).
Nacka et al., "Induction of New Physiochemical and Functional Properties by the Glycosylation of Whey Proteins," *J. Protein Chem.*, 17:495-503 (1998).
Prabakaran and Damodaran, "Thermal Unfolding of β-Lactoglobulin: Characterization of Initial Unfolding Events Responsible for Heat-Induced Aggregation," *J. Agric. Food Chem.*, 45:4303-4308 (1997).
Petrovsky et al., "New-Age Vaccine Adjuvants: Friend or Foe," *Biopharm International*, pp. 24-33 (2007).
Ralston, "Effects of 'Crowding' in Protein Solutions," *J. Chem. Educ.*, 67:857-860 (1990).

(56) References Cited

OTHER PUBLICATIONS

Sano et al., "Astringency of Bovine Milk Whey Protein," *J. Dairy Sci.*, 88:2312-2317 (2005).

Sarni-Machado et al., "Influence of the Glycosylation of Human Salivary Proline-Rich Proteins on Their Interactions with Condensed Tannins," *J. Agric. Food Chem.* 56: 9563-9569 (2008).

Schmitt et al., "Kinetics of Formation and Functional Properties of Conjugates Prepared by Dry-State Incubation of β-Lactoglobulin/Acacia Gum Electrostatic Complexes," *J. Agric. Food Chem.*, 53:9089-9099 (2005).

Sengupta and Damodaran, "A New Methodology for Studying Protein Adsorption at Oil-Water Interfaces," *J. Colloid Interface Sci.*, 206:407-415 (1998).

Somalinga and Roy, "Volume Exclusion Effect as a Driving Force for Reverse Proteolysis," *J. Biol. Chem.*, 277:43253-43261 (2002).

Tamaoka et al., "High Pressure Effect on Maillard Reaction," *Agric. Biol: Chem.*, 55:2071-2074 (1991).

Tanaka et al., "Improvement of Emulsifying and Antibacterial Properties of Salmine by the Maillard Reaction with Dextran," *Fisheries Sci.*, 65:623-628 (1999).

Vallejo-Cordoba and Gonzalez-Cordova, "CE: A Useful Analytical Tool for the Characterization of Maillard Reaction Products in Foods," *Electrophoresis* 28:4063-4071 (2007).

Wang and Lucey, "Use of Multi-Angle Laser Light Scattering and Size-Exclusion Chromatography to Characterize the Molecular Weight and Types of Aggregates Present in Commercial Whey Protein Products," *J. Dairy Sci,*. 86:3090-3101 (2003).

Zhu et al., "Formation of Whey Protein Isolate (WPI)—Dextran Conjugates in Aqueous Solutions," *J. Agric. Food Chem.*, 56:7113-7118 (2008).

International Search Report dated Aug. 3, 2009 received in related PCT Application No. PCT/US2009/037660.

\* cited by examiner

PRODUCTION OF PROTEIN-POLYSACCHARIDE CONJUGATES

CROSS-REFERENCE TO RELATED APPLICATIONS

This is a continuation of U.S. patent application Ser. No. 12/407,543, filed Mar. 19, 2009, which claims priority to U.S. Provisional Patent Application Ser. No. 61/037,912, filed Mar. 19, 2008, which is incorporated herein by reference.

GOVERNMENT INTERESTS

This invention was made with government support under 2004-35503-14839 awarded by the USDA/NIFA. The government has certain rights in the invention.

FIELD OF THE INVENTION

The present invention relates generally to the field of protein-polysaccharide conjugates.

BACKGROUND

Food proteins and polysaccharides (PS) are two key structural components used to control texture, structure, and stability of food materials. Typically, foods contain both biopolymers in the form of complex multicomponent mixtures. Conjugation of protein with polysaccharide has been intensively studied in recent years (Dunlap and Côté, 2005, *J. Agric. Food Chem.* 53: 419-423), with a significant improvement in functional properties (e.g. solubility and heat stability) over a wide pH range.

Protein-polysaccharide conjugates (PPC) (i.e., proteins covalently linked to polysaccharides) are useful as emulsifiers in foods and beverages. The addition of the polysaccharide stabilizes the protein, and such protein-polysaccharide conjugates have superior functional properties (e.g., gelation, emulsification, solubility, heat/pH stability) compared to the unaltered proteins. A naturally produced protein-polysaccharide conjugate can be found in gum arabic, which contains about 2% covalently bound protein. Gum arabic is used extensively as a natural food emulsifier/stabilizer for emulsions and beverages, as an encapsulation agent for flavor delivery, in gum drops and similar candies, and to control ice crystallization in frozen products. However, the price and availability of gum arabic is extremely volatile due to a variety of growth, harvest, and regional issues. About half of the gum arabic produced worldwide is imported by the US (approximately 30,000 tons). Consequently, there is considerable commercial interest in developing a substitute for gum arabic.

Two main techniques are used to produce covalently linked protein-polysaccharide conjugates: (1) chemical modification using reagents such as carbodiimide, and (2) glycation by exploiting the initial step (i.e., Schiff base step which is well before the browning and other undesirable reactions) of the Maillard reaction between a reducing sugar (e.g., glucose, lactose) and an amino group (e.g., lysine). Chemical modifications usually use toxic reagents that are not desirable for use in food ingredients. The usual glycation procedure involves using dry heating (e.g., 60° C.), and storage of the lyophilized mixtures (protein and PS) for a period of up to several weeks at a specific relative humidity (RH).

The initial step in the Maillard reaction, the formation of a covalent linkage between $\varepsilon\text{-NH}_2$ amino groups on proteins and carbonyl groups on reducing sugars, has been used to create new ingredients with improved food functionalities. The Maillard reaction is comprised of a complex series of reactions, which simultaneously occur by multiple reaction pathways. Generally, the Maillard reaction occurs in three stages (Hodge, 1953, *J. Agric. Food Chem.* 1: 928-943). The initial stage consists of the condensation between $\varepsilon\text{-NH}_2$ amino groups and carbonyl groups, Schiff base formation and irreversible Amadori rearrangement, which leads to the Amadori products. The products at this initial stage are colorless, and there is no absorption in the near-ultraviolet spectrum. The intermediate stage involves sugar dehydration, sugar fragmentation and amino acid degradation. These products result in absorption at 277-285 nm due to the furfural region (Vallejo-Cordoba and Gonzalez-Cordova, 2007, *Electrophoresis* 28: 4063-4071; Hodge, 1953, *J. Agric. Food Chem.* 1: 928-943). Products are colorless or yellow in the intermediate stage. The final stage is highly colored (yellow or brown), with the formation of brown pigments called melanoidins.

The conjugation of proteins with polysaccharides (PS) is usually carried out using dry-heat treatment, for example the conjugation of β-lactoglobulin (β-Lg) and dextran, under conditions of about 60° C., 35-40% RH (relative humidity), for about 3 weeks (Dickinson and Galazka, 1991, *Food Hydrocoll.* 5: 281-296). However, there are several disadvantages for this method. It requires powdered protein and PS materials and a constant temperature and relative humidity (e.g., 79% RH), which must be maintained during the reaction. The time required for the reaction is also significant (e.g., 3-5 weeks at 60° C.). The reaction process also cannot be easily controlled and the products are complicated. Intermediate or final stage products of the Maillard reaction are also typically obtained as indicated by the appearance of undesirable light yellow or brown color, which results in increased absorbance at ≥420 nm (Dickinson and Galazka, 1991; Tanaka et al., 1999, *Fisheries Sci.* 65: 623-628). Although the conjugation of proteins with PS by the dry heating process has resulted in interesting improvements in functional properties, the dry-heat treatment method is not attractive and, as a result of the significant disadvantages described above, there are few commercial PPC ingredients.

Whey proteins, including β-Lg, have been used to stabilize food emulsions because of their surface active properties (Dickinson, 1997, *J. Dairy Sci.* 80: 2607-2619). The emulsifying properties of PPC prepared with whey proteins by the dry heating process have been studied extensively. While many types of PS have been tested by this dry heating process little is known about the effect of the molecular weight size of the PS on the properties of the PPC.

To use the Maillard conjugation type of approach to commercially produce viable food ingredients, new methods are needed to induce this reaction in a short processing time and in aqueous protein-PS mixtures instead of the expensive lyophilized samples that have been previously studied. It would be advantageous to formulate new ingredients (e.g., PPC) that provide improved functionality (e.g., emulsion stability) and health benefits in various nutritional products (e.g., reduced allergenicity in infant formulae and reduced astringency in low pH protein-fortified beverages). The present invention addresses these and related needs.

BRIEF SUMMARY

Methods of preparing polysaccharide-protein conjugates are provided. The methods include: reacting polysaccharides comprising a reducing sugar and proteins in an aqueous solution comprising 10-40% (w/v) polysaccharide and 1-30% (w/v) protein, under temperature conditions of from about 40° C. to about 120° C., thereby producing polysaccharide-protein conjugates. In the practice of the methods, the solutions may be acidified to a pH from about 6.0 to about 8.0. The reducing sugar and the proteins may be reacted under temperature conditions of from about 40° C. to about 120° C. for a period of from about 1 hour to about 48 hours. The solutions may be subjected to a hydrostatic pressure in the amount of between about 1 MPa and about 20 MPa. The methods may further include recovering of the polysaccharide-protein conjugates from the solutions in various ways, for example including chromatography. Detection of the polysaccharide-protein conjugates may be performed by difference UV spectroscopy. The difference UV spectroscopy may include measuring absorbance of the polysaccharide-protein conjugates at a wavelength of 304 nm. In the practice of the methods, the proteins may be, for example, soy proteins, or they may be caseinates. Methods of emulsification, comprising using as emulsifiers the above polysaccharide-protein conjugates are also provided.

Methods for producing whey protein isolate (WPI)-dextran conjugates are provided. The methods include: reacting dextran and whey protein isolate in an aqueous solution comprising 10-40% (w/v) dextran and 1-30% (w/v) protein, under temperature conditions of from about 40° C. to about 120° C., thereby producing whey protein isolate-dextran. In the practice of the methods, the solutions may be acidified to a pH from about 6.0 to about 8.0. The whey protein isolate and the dextran may be reacted under temperature conditions of from about 40° C. to about 120° C. for a period of from about 1 hour to about 48 hours. The solutions may be subjected to a hydrostatic pressure in the amount of 1-20 MPa. The methods may include the steps of recovering the whey protein isolate-dextran conjugates from the solutions, for example including chromatography. Detection of the whey protein isolate-dextran conjugates may be performed by difference UV spectroscopy. The difference UV spectroscopy may include measuring absorbance of the whey protein isolate-dextran conjugates at a wavelength of 304 nm. Whey protein isolate-dextran conjugates which are obtained by these methods are provided. Methods of emulsification, comprising using as emulsifiers the above whey protein isolate-dextran conjugates are also provided.

Polysaccharide-protein conjugates are provided, where the conjugates are comprised substantially of Schiff base. The conjugates may be substantially free of intermediate and advanced Maillard products. The conjugates may be white in color, and they may maintain the white color for a period of at least three months. The conjugates are able to produce fat globules during homogenization that are of small particle size, e.g. the fat globules may be less than about 2 µm in diameter. The conjugates may be thermostable for a period of at least 3 weeks in solutions that are held at about 5° C. The stability of the emulsion can be determined by the lack of a large change in particle size during storage of the emulsion.

Emulsifying compositions and methods of emulsification are provided. The emulsifying compositions and the methods include using as emulsifying compositions the polysaccharide-protein conjugates of the present invention.

Food compositions with alleviated astringency and methods of alleviating astringency of proteins are provided. The food compositions and the methods include using as astringency alleviating compositions the polysaccharide-protein conjugates of the present invention.

Food compositions with reduced allergenicity and methods of producing food compositions with reduced allergenicity are provided. The food compositions with reduced allergenicity and the methods include using as reduced allergenicity compositions the polysaccharide-protein conjugates of the present invention.

DETAILED DESCRIPTION OF THE PRESENTLY PREFERRED EMBODIMENTS

Figure 1:
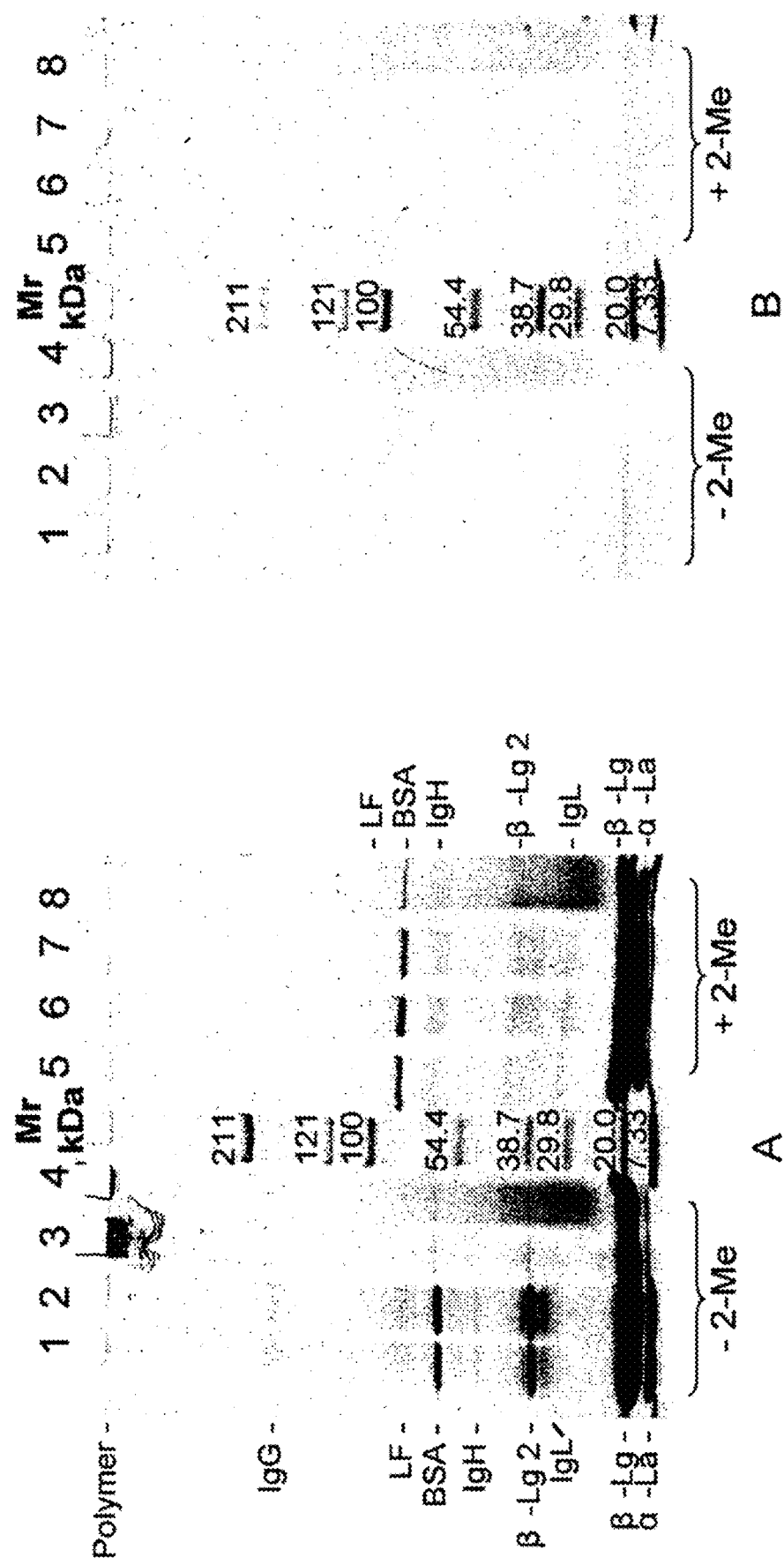
FIG. 1 shows images of SDS-PAGE of WPI-dextran conjugates in the absence (lanes 1-4) and presence (lanes 5-8) of 5% of 2-mercaptoethanol. Panel A: protein stain (Coomassie blue). Panel B: carbohydrate stain (periodic acid). Mr: molecular weight standards. Lanes 1 and 5, 10% WPI (unheated). Lanes 2 and 6, mixture of 10% WPI-30% dextran (unheated, pH 6.5, 60° C., 24 h). Lanes 3 and 7, 10% WPI (pH 6.5, 60° C., 24 h). Lanes 4 and 8, mixture of 10% WPI-30% dextran (pH 6.5, 60° C., 24 h).

In one aspect, the present invention relates to protein-polysaccharide conjugates (PPC) and to methods of preparing same. In one example, the present invention provides novel methods to produce protein-polysaccharide conjugates using an aqueous solution and using a wet heat treatment. The invention is particularly well-suited for producing protein-polysaccharide conjugates that may be used as emulsifiers.

"Aqueous solution" means a solution in which the solvent is primarily water.

"Protein" means organic compounds made of amino acids arranged in a linear polymeric chain and joined together by peptide bonds between the carboxyl and amino groups of adjacent amino acid residues.

"Polysaccharides" means complex carbohydrate polymers comprising multiple monosaccharide units joined together by glycosidic bonds. Polysaccharides have a general formula of $C_n(H_2O)_{n-1}$ where n is usually a large number between 200 and 2500.

"Protein-polysaccharide conjugates" (PPC) refers to proteins covalently linked to polysaccharides.

"Reducing sugar" means any sugar that, in basic solution, forms an aldehyde or ketone. This allows the sugar to act as a reducing agent, for example in the Maillard reaction. Reducing sugars include, but are not limited to, glucose, fructose, glyceraldehyde, lactose, arabinose and maltose, maltodextrin, dextran.

"Dextran" means a complex, branched polysaccharide comprising multiple glucose molecules joined into chains of varying lengths (from 10 to 150 kDa). The straight chain consists of α1->6 glycosidic linkages between glucose molecules, while branches begin from α1->4 linkages (and in some cases, α1->2 and α1->3 linkages as well).

"Dextrin" means a low-molecular-weight carbohydrate produced by the hydrolysis of starch. Dextrins are mixtures of linear α-(1,4)-linked D-glucose polymers starting with an α-(1,6) bond. An example of dextrins is maltodextrin, a polysaccharide that is used as a common food additive.

"Schiff base" (or azomethine), named after Hugo Schiff, means a functional group that contains a carbon-nitrogen double bond with the nitrogen atom connected to an aryl or alkyl group—but not hydrogen. Schiff bases are of the general formula $R_1R_2C=N-R_3$, where $R_3$ is an aryl or alkyl group that makes the Schiff base a stable imine. In one example the methods of the present application may be used to control the extent of the Maillard reaction to stop at the initial Schiff base formation. Identification and/or quantification of Schiff base can be performed spectroscopically and/or calorimetrically.

Methods to produce protein-polysaccharide complexes using wet heat treatment are provided. In contrast to previous work on PPC made by the dry heating process, the present invention contemplates the use of aqueous solutions to prepare PPC. These aqueous solutions may be aqueous mixtures. In one example the methods involve heating aqueous solutions of relatively high concentrations of protein (e.g., 1-30%, preferably 5-20%, and more preferably about 10% w/v protein) in the presence of relatively high concentrations of a polysaccharide with a reducing sugar (e.g., 10-40%, preferably 20-35%, and more preferably about 30% w/v polysaccharide). The polysaccharide may include one type of monosaccharide unit (it may be a homopolysaccharide). Alternatively, the polysaccharide may include more than one type of monosaccharide unit (it may be a heteropolysaccharide).

A variety of proteins may be used for practicing the present invention. Useful proteins will preferably have one or more lysine residues. In one example, there is a minimum of one lysine reside per protein molecule. One lysine molecule may be sufficient to bind to one polysaccharide group, thereby creating a conjugate. In some examples, the proteins used in the practice of the present invention have relatively small molecular weight. Non-limiting examples of proteins useful for practicing the present invention include a variety of proteins with molecular weights in the range of about 11,000 Da to about 500,000 Da. The proteins may include whey proteins (e.g. whey protein isolate, WPI), caseins (caseinates), soy proteins, etc. The amounts of WPI may vary, and in some examples the concentration of WPI that is used for practicing the present invention is typically in the range of about 1-30% (w/v), and preferably the amounts of WPI are in the range of 5-20% (w/v). In one example, conjugates are formed in reactions that use starting aqueous solutions of about 10% (w/v) WPI. As well, a variety of sugars (saccharides), preferably with one or more types of reducing terminal, may be used for practicing the present invention. Examples of sugars that can be used for practicing the present invention include: monosaccharides (e.g., glyceraldehyde; arabinose; ribose; xylose; galactose, glucose, mannose; fructose); disaccharides (e.g., lactose; maltose); polysaccharides (e.g., galactomannans; dextran; maltodextrin; chitosan; alginic acid; agar; carrageenan; dextran sulfate; konjac mannan; xyloglucan; starch; modified starches; pectins; dietary fiber, such as polydextrose, wheat dextrin, oat bran concentrate). In some examples, the polysaccharides useful for practicing the present invention may include aqueous solutions of about 20-40% (w/v) dextran or about 20-40% (w/v) maltodextrins, preferably about 30% (w/v) dextran or about 30% (w/v) maltodextrin. The choice of polysaccharide influences the concentration of polysaccharide (w/v) used in the conjugation reaction. The concentration of polysaccharide influences the viscosity of the aqueous polysaccharide solution.

In some examples, to provide the mixture where the conjugation reaction takes place, protein and polysaccharide may be provided as aqueous solutions. Solvent may also be provided as necessary, to adjust the concentrations of each of the protein and the polysaccharide to desired values (w/v). Aqueous solutions of protein and of polysaccharide may be added simultaneously, or they may be added sequentially. Once protein and polysaccharide have been combined to create a mixture, the pH of the mixture solution may be adjusted to a desired value using acids and/or bases.

Protein denaturation is a function of the temperature and the pH of the aqueous solution where the protein is located. While higher temperature may generally accelerate the conjugation reaction, higher temperature also may cause heat denaturation of the proteins. For some non-globular proteins like caseins there is no real denaturation temperature and higher processing temperatures can be used compared with globular proteins. For example, the conjugation reaction is promoted by raising the temperature from 20° C. to 70° C. Not wanting to be bound by the following theory, it is believed that the elevated concentration of polysaccharide may protect the protein from heat denaturation. The polysaccharides may act not only as a reactant taking part in the conjugation, but also as a protective reagent in preventing excessive protein denaturation and/or aggregation. Not wanting to be bound by the following theory, it is believed that high polysaccharide concentration may also "crowd" the protein promoting the conjugation reaction. In some preferred embodiments, polysaccharide such as dextran may be used as a crowding agent, while another type of reducing sugar may be used to drive the reaction. Alternatively, or in addition to dextran, other crowding agents may be used instead of polysaccharides. Examples of crowding agent useful in the practice of the present invention include, but are not limited to, ficolls, dextrans, polyethylene glycol, polyvinyl alcohol, bovine serum albumin, and poly(vinylpyrrolidone).

The conjugation reactions may be carried out under controlled temperature conditions. For example, the conjugation reaction may be carried out using temperatures in the range of about 40° C. to about 120° C., and more preferably in the range of about 50° C. to about 70° C. In one example, the conjugation reaction may be carried out using a temperature of about 65° C. Higher temperatures are used for proteins that have higher denaturation temperatures than the WPI used in this example.

In one example, the conjugation reaction of the present invention may be influenced by controlling the pH of the reaction solution. Higher (more alkaline) pH values can shorten the time of the conjugation reaction. For example, for WPI the conjugation reaction is promoted by lowering the pH from 8.5 to 5.5. It is believed that high pH values promote disulfide protein interactions in whey proteins, which is undesirable for the conjugation reaction.

In general, the specific temperatures and pH values for the conjugation reaction will depend on the particular protein used. The duration of the reaction may also depend on the particular protein used. For example, caseins are not very sensitive to heat denaturation so it is possible to use relatively high temperatures and relatively high pH as well, and thus obtain PPC in a shorter time. In such examples, when caseinate is the reacted protein, higher temperatures and different pH conditions can be used, e.g. temperatures for the conjugation reaction can be in the range of from about 40° C. to about 110° C., the reaction can be conducted for between 30 min to 4 hours, and the pH values can vary between about 6.0 to about 8.5.

Hydrostatic pressure treatment may be used to control the conjugation reaction. For example, protein-polysaccharide mixtures may be pressurized at 2-20 MPa, preferably at about 7.9 MPa, by subjecting the mixtures to pressure provided by cylinders of compressed nitrogen gas.

Once the proteins and the polysaccharides are mixed together, the conjugation reactions may be carried out for various periods of time. The duration of the reaction influences the yield of product, such as the conjugate. It is contemplated that generally the conjugation reactions of the present invention are carried out for a period of time of between 1 and 96 hours, and more preferably the conjugation reactions of the present invention are carried out for a period of time of about 6 to about 24 hours.

The conjugates produced according to the present invention may be used directly, without purification. Thus, the entire mixture may be used, for example as a food ingredient.

The methods of the present invention can be used to attach biologically important carbohydrates to proteins for desired nutritional and/or bioactivity purposes.

Optionally, the conjugates of the present invention may be purified. The resulting conjugates may be purified using methods known in the art, for example using chromatographic methods. Thus, PPC may be purified using anion exchange chromatography and size exclusion chromatography (Dunlap and Côté, 2005, *J. Agric. Food Chem.* 53: 419-423) and/or affinity chromatography. In one example, the method of the present invention provide for obtaining substantial quantities of purified conjugates for use in foods. The present invention also provides spectroscopic methods for monitoring the progress of the conjugation reactions and chromatographic methods for purifying the conjugates (conjugate complexes). In practice, purification of conjugates is not required if the reaction mixture is used as an ingredient.

To assist in the process for conjugating a protein and a polysaccharide, a crosslinker or a spacer can be provided on either the protein or the polysaccharide. Because the crosslinker is a smaller molecule, it helps the coupling reaction for the larger protein and polysaccharide molecules proceed more quickly by allowing better access to the large molecules, and thereby enhancing the reactivity. Additionally, the use of a crosslinker allows one to more effectively control the degree of crosslinking and the chemical structure of the resultant conjugate.

Various procedures and chemistries are available for activating and attaching spacers to proteins and to polysaccharides, e.g., using CDAP, carbodiimides, NHS esters, CNBr, and carbodiimide. Published PCT Patent Application No. WO/1997/041897, incorporated herein by reference, describes the use of vinylsulfones as the reactive group in a crosslinking agent.

The methods of the present invention may be practiced using aqueous solutions and mixtures in a variety of volumes. For example, conjugation reactions may be performed in various vessels, beakers, tanks, etc. The methods of the present invention may be practiced using batch processing.

The resulting purified conjugates (PPC) exhibit improved thermal stability, more desirable color (white as opposed to yellow or brown), and excellent emulsifying properties that are superior to both the unmodified whey protein and the gum arabic. White color means having the color of pure snow or milk, the color of radiated, transmitted, or reflected light containing all of the visible rays of the spectrum; opposite to black. The white color of the PPC conjugates of the present invention is stable and is maintained for months. In contrast, comparable compositions of conjugates that include other sugars turn darker within days of synthesis, exhibiting non-white, darker, yellow or brown color.

The conjugates according to the present invention are able to produce fat globules during homogenization that are of a small particle size, e.g. less than about 2 µm in diameter. The conjugates may be thermostable for a period of at least 3 weeks in solutions held at about 5° C. The stability of the emulsion can be determined by the lack of a large change in particle size during storage of the emulsion. For example, the denaturation temperature of the conjugates is about 87° C. by the determination using Differential Scanning calorimetry (DSC), which is much higher than the denaturation temperature of Whey Protein Isolate, which is about 72° C.

The compositions produced according to the present invention, such as unfractionated reaction mixtures containing PPC or the purified PPC, may function as superemulsifiers, i.e. emulsifiers with properties superior to gum arabic. Not wanting to be bound by the following theory, it is possible that the steric stability is conferred by the bulky PS while the attached protein is able to give the hydrophobic/hydrophilic character necessary to stabilize the emulsion interface. The conjugates may significantly decrease the interfacial tension, and improve the solubility at severe heat treatments, lower pH, and higher salt concentration than whey protein. One possible use of these emulsifiers is as fat replacers in low-fat foods. The conjugates may possess the following emulsifying properties: a whey protein-dextran conjugate, made from dextran (molecular weight 500,000 kDa), is capable of producing fine emulsion droplets (0.25 µm diameter) with soybean oil, whereas the equivalent emulsion made with gum arabic produces droplets of 0.56 µm and WPI produces droplets of 0.31 µm. The emulsion stabilized by conjugates of the present invention is stable over a storage period of at least up to 8 weeks, with no visible precipitation or phase separation, but emulsion made using whey protein or Gum Arabic is not stable over such period of time. Examples of methods for measuring emulsifying properties and determining the stability of emulsions are found below.

The compositions produced according to the present invention may alleviate astringency of proteins. "Astringency" refers to a complex group of sensations involving dryness, roughness of oral surfaces and tightening, drawing or puckering of the mucosa and muscles around the mouth. Astringency has been attributed primarily to interactions between the salivary proline-rich-proteins (SPRP) and other compounds that have a particularly high affinity for the SPRPs, such as polyphenols. Attachment of dextran onto a protein molecule could interfere with the reaction between proteins with salivary proteins and their precipitation. This could reduce the sensation of protein astringency in low pH environments (e.g. as in protein fortified acid beverages). Conjugation of proteins alters their solubility (increases it) and also their charge both of which could influence possible reactions with salivary proteins. For example, glycosylated salivary proteins-tannin complexes lead to a lower astringency perception (Sarni-Machado et al., 2008, *J. Agric. Food Chem.* 56: 9563-9569). Astringency of the compositions of the present invention can be measured, e.g., using the methods described in Beecher et al., 2008, *J. Dairy Sci.* 91: 2553-2560. Examples of methods for determining astringency of proteins are found below.

The compositions produced according to the present invention may be useful in processing proteins such as whey protein isolate to make it less allergenic. Food allergy encompasses a group of disorders characterized by immunologic responses to food proteins. For example, conjugation of milk proteins with dextran may reduce their allergenicity by interfering with recognition sites on proteins that cause elevation of IgE. The reduced allergenicity of WPI may be of interest, for example, to infant formula manufacturers. Examples of methods for determining reduced allergenicity are found below.

The term "reduced allergenicity" indicates that the amount of produced IgE (in humans, and molecules with comparable effects in specific animals), which can lead to an allergic state, is decreased when consuming the protein-polysaccharide conjugates of the invention in comparison to comparable protein-polysaccharide conjugates obtained according to other methods known in the art.

The compositions produced according to the present invention may be useful in the incorporation of "biologically functional" carbohydrate/polysaccharide groups, e.g. groups that may confer the sensation of satiety (fullness after consumption, reducing appetite).

The compositions produced according to the present invention provide low cost and plentiful emulsifying agents for food products (e.g., salad dressings, gum, gummy candies, frozen foods, etc.) and beverages (e.g., Coke); substitute for gum arabic. Examples of whey protein emulsifiers and emulsions are described, for example, in published PCT Patent Application No. WO/2006/090110 A1, which is incorporated herein by reference.

The compositions produced according to the present invention may be used as vaccine adjuvants, using for example the approaches described in Petrovsky et al., Aug. 1, 2007, *Biopharm*, pp. 24-33; and in U.S. Pat. No. 6,573,245.

In one example, WPI-dextran conjugates can be formed in mixtures of 10% WPI-30% dextran during incubation at pH 6.5 and 60° C. for 24 h. The conjugation of WPI and dextran can be confirmed using a variety of methods known in the art, including, for example, by SDS-PAGE with both protein staining and carbohydrate staining. The WPI-dextran conjugate can be further identified to be mainly composed of Schiff base, which is characterized by a maximum absorbance peak values at 304 nm by DUV. Hydrostatic pressure (7.9 MPa) can promote the conjugation at certain pH values (e.g., at 7.0), but it can suppress the conjugation at other pH values (e.g., at 6.5).

Methods to limit the Maillard reaction to the very initial stage, the formation of the Schiff base, are also provided. Controlling the extent of the Maillard reaction has the advantage of limiting the formation of unwanted intermediates or advanced products. Using the present methods it is possible to obtain a simple product that is comprised substantially of Schiff base with white color and with relatively high thermal stability (denaturation temperature 88° C.) in comparison to the native whey protein (denaturation temperature 74° C.). Thus, in one aspect, the compositions of the present invention remain at the Schiff base level. Measurable amounts of Schiff base can be obtained relatively rapidly, within about 1.5-2 hours of the beginning of the reaction.

In comparison to existing methods, the methods of the present invention offer improved protection against protein aggregation, allowing for the use of higher treatment temperatures. The methods of the present invention require less time and energy than the dry heating method. The resulting purified protein-polysaccharide conjugate obtained according to present invention exhibits improved thermal stability, more desirable color, and excellent emulsifying properties that are superior to both the unmodified whey protein and the gum arabic. Some comparative advantages of the novel methods in accordance with the present invention are outlined in Table 1 below. In Table 1, PS refers to polysaccharides; PPC refers to protein-polysaccharide conjugates.

TABLE 1

Some comparative advantages of the present invention (wet-heat treatment) relative to the conventional dry-heat treatment method

| CONDITIONS | WET-HEAT TREATMENT (present invention) | CONVENTIONAL DRY-HEAT TREATMENT |
|---|---|---|
| Type of materials needed for the reaction | Aqueous solutions of both protein and PS materials | Dried powdered mixtures of each material |
| Humidity requirements | No specific humidity requirement | Maintain constant temperature (e.g., 80° C.) and relative humidity (e.g., 79° C.) |
| Reaction time and temperature | From 4 to 24 hours (60-70° C.) | 3-5 weeks (60° C.) |
| Type of products formed in the reactions | Products are almost completely composed of Schiff base | Products are a complex mixture of Intermediate and Advanced Maillard products |
| Color of PPC or reactions mixture | Products are white in color | Products have a yellow or brown color |
| Level of protein denaturation | Little protein denaturation or aggregation occurs during reaction, stabilized by high [PS] | Unknown how much protein denaturation occurs during reaction (not usually determined) |

Some embodiments of the present invention are described in Zhu et al., 2008, *J. Agric. Food Chem.* 56: 7113-7118, which is herein incorporated by reference.

EXAMPLES

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Materials

Whey Protein Isolate (WPI) was provided by Davisco Foods International, Inc. The total amount of protein in the dry powder was >95% and the lactose was low (<1%). Before use, WPI was dissolved in Milli-Q water and thoroughly dialyzed against Milli-Q water (dialysis membrane tubing had a molecular weight cut-off of 6,000-8,000 Da) for 3 days at 5° C. with changes in water every 6 h to remove lactose. After lyophilization, purified WPI was stored at 5° C. prior to its use.

Dextran (Batch #115k0686, CAS 9004-54-0) from *Leuconostoc mesenteroides*, with molecular weight 8,500-11,500 (11 kDa), was obtained from Sigma-Aldrich (St. Louis, Mo.). Before use, dextran was dissolved in Milli-Q water and dialyzed against Milli-Q water for two days at 5° C. with changes in water every six hours. The dialysis membrane tubing had a molecular weight cut-off of 3,000 Da (Fisher Scientific, Pittsburgh, Pa.). After lyophilization, purified dextran was stored at 5° C.

Prestained SDS-PAGE molecular weight standards (Broad range) were purchased from Bio-Rad Laboratories (Hercules, Calif.). The GelCode glycoprotein staining kit was purchased from Pierce Biotechnology (Rockford, Ill.).

Preparation of Conjugates by Heat Treatment

Mixtures of WPI-dextran in various ratios (by weight) were dissolved in 10 mM sodium phosphate buffer (NaPi) solution (pH 6.8). Sodium azide (0.02%, w/w) was added to prevent bacterial growth. The sample solutions were stirred on a magnetic stirrer at room temperature (18 22° C.) for 2 h to completely dissolve the mixture. The pH values of the solutions were adjusted by carefully adding 0.1 N HCl or 0.1 N NaOH to the desired pH. Solutions were gently stirred overnight at 5° C. to ensure the complete hydration of the macromolecules. Aliquots of the solutions (1.0 ml, dispensed into 1.5 ml eppendorf tubes) were placed in a water bath heated at various temperatures for 24 h. Samples were then taken out of the water-bath and immediately cooled down at ice-water bath. Triplicates were carried out for each experiment.

Time Course of the Reaction

Using the same heat treatment for the sample preparation, a number of sample solutions were incubated at 60° C. for different time periods. The sample solutions typically included WPI-dextran, and more typically 10% WPI-30% dextran, at pH 6.5. At each time point, three sample tubes were taken out from the water bath and immediately cooled down at ice-water bath before analysis. Triplicate experiments were performed.

Formation of Conjugates under Hydrostatic Pressure Treatment

Sample solutions of WPI-dextran (12 ml) mixtures prepared as described above were transferred into a pressure cell of a rheometer (Universal Dynamic Spectrometer, Paar Physica UDS 200 Physica Messtechnik GmbH, Stuttgart, Germany). Pressurization (up to maximum of 7.9 MPa) was achieved by connecting the cell to a cylinder of compressed nitrogen gas. No shearing was applied. Temperature and time were controlled by the software attached to the rheometer. Three replicates were performed for each sample; and three measurements were done for each replicate.

Sodium Dodecyl Sulfate-Polyacrylamide Gel Electrophoresis (SDS-PAGE)

SDS-PAGE was performed on a Mini-Protean 3Cell (Bio-Rad Laboratories) by the method of Laemmli (Laemmli, 1970, *Nature* 227: 680-685). Non-reducing and reducing SDS-PAGE analyses were carried out on a ready gel (TRIS-HCl Gel, 4-20% linear gradient, 15 well, Bio-Rad Laboratories). Sample solution (15 µl corresponding to 40 µg of whey protein) was loaded into each well. Electrophoresis was run for 35 min at 200 V in 0.025 M Tris-HCl buffer solution (pH 8.3, including 0.192 M glycine and 0.1% SDS, w/w) at room temperature. Two gels were run at the same time. After electrophoresis, one gel was stained for protein by Coomassie blue G-250 and the other one was stained for carbohydrate by the GelCode Glycoprotein staining kit (Pierce Biotechnology), respectively. The protein stain was destained with 10% acetic acid (v/v) containing 30% methanol (v/v).

Difference UV Spectroscopy (DUV)

DUV measurements were carried out on a UV-visible spectrophotometer (Shimadzu UV-1601 PC, Shimadzu Corporation, Kyoto, Japan), in a 1-cm quartz cell at a constant temperature of 20° C. The samples were diluted 33.3-fold, followed by centrifugation at 16,000×g for 10 min in an Eppendorf Centrifuge (Model 5414, Brinkmann Instruments Inc., Westbury, N.Y.) at room temperature. The supernatant was used for a wavelength scan from 270 to 500 nm. The difference absorption spectra of conjugates after processing were recorded against an un-reacted sample, which was used as a reference. The extent of conjugation was assessed by the DUV absorbance peak value at about 304 nm (Blonski et al., 1997, *Biochem. J.* 323: 71-77).

Appearance of WPI-Dextran Conjugates

When solutions of 10% WPI-30% dextran (pH 6.5) were incubated at 60° C. for 24 h, the solutions in the eppendorf tube appeared white and opaque. There was no obvious aroma or smell, nor was any significant change in viscosity observed within the 24 h incubation period. When the sample was centrifuged at 16,000×g for 30 min, the supernatant appeared clear, translucent, and the precipitate was white. The supernatant, where the conjugate resided, was typically used for the analyses described herein.

To determine if the precipitate was protein or dextran, aliquots of the precipitate were subjected to several tests. The precipitate hardly dissolved in 8 M urea or 10% SDS either in the absence or presence of 2-mercaptoethanol. These observations made it unlikely that the precipitate was denatured WPI proteins. Dextran self-associates in sufficiently concentrated solutions, and these dextran associates can be dissolved when re-suspended in distilled water and autoclaved for 30 min (Cadwallader et al., 1958, *J. Amer. Pharm. Assoc.* 47: 894-895). When the obtained white precipitate was re-suspended in Milli-Q water (4-10%), the precipitate apparently dissolved when heated at 100° C. for 30 min. This indicated that the white precipitate was due to the association of dextran.

With prolonged incubation time (>24 h), a strong aroma was noted, and a yellow color appeared. The reaction was typically stopped after 24 h incubation by rapidly cooling down the samples in an ice-water bath.

WPI-Dextran Conjugate Interaction Studied by SDS-PAGE

The reaction between WPI and dextran was investigated by SDS-PAGE. As shown in FIG. 1 (protein stain), under non-reducing conditions (lanes 1-4 in FIG. 1A), unheated WPI (native WPI, lane 1, FIG. 1A) and the mixture of 10% WPI-30% dextran (5° C. for 24 h, lane 2, FIG. 1A) had identical and characteristic bands of WPI. As identified in FIG. 1, two major bands were assigned to monomers of α-La and β-Lg respectively; two minor bands were attributed to dimers of β-Lg and BSA; and the four faint bands were LF, IgG, IgL and IgH. This indicated that no polymerization occurred in WPI in the presence of 30% dextran without heat treatment of the mixture. For the heat-treated 10% WPI alone (lane 3, FIG. 1A), the α-La, β-Lg dimer, BSA and IgG bands were significantly diminished; the intensity of the β-Lg monomer band was reduced; meanwhile a dense band appeared on the top of the gel. This indicated that proteins in WPI had associated into large molecular polymers that could not migrate into the separating gel. In the case of heat-treated mixture of 10% WPI-30% dextran (lane 4, FIG. 1A), a new diffuse band that had a molecular weight distribution of 26-98 kDa appeared in the separating gel, indicating the formation of new protein species, which migrated into the separating gel. In addition, a thin band of large molecular weight polymers was observed on the top of the gel similar to the heated 10% WPI sample. Compared to the heated 10% WPI sample alone (lane 3, FIG. 1A), the intensity of the band with large molecular weight polymers was less intense in the heated mixture of 10% WPI-30% dextran (lane 4, FIG. 1A). This indicated that the polymerization of WPI was greatly inhibited in the presence of 30% dextran. A similar phenomenon was reported by Schmitt et al., 2005, *J. Agric. Food Chem.* 53: 9089-9099, where the polymerization of β-lactoglobulin was greatly reduced by the presence of acacia gum. Garrett et al., 1998, *J. Dairy Sci.* 71: 10-16, suggested that the inhibition of the thermal aggregation of whey proteins by various sugars was caused by reducing hydrophobic intermolecular interactions between protein molecules.

Since non-covalent interactions were dispersed during SDS-PAGE, the new protein species and the large molecular weight polymers on the top of the gel in lane 4 (FIG. 1A) were linked by some types of covalent bonds. Under reducing conditions, for lanes 7 and 8 (FIG. 1A), the large molecular weight polymers which resided at the top of lanes 3 and 4 (FIG. 1A) completely disappeared, indicating that these large polymers were linked by disulfide bonds. The heated 10% WPI under reducing conditions (lane 7, FIG. 1A) had identical bands compared to native WPI (unheated, lanes 5 and 6, FIG. 1A), while the heated mixture of 10% WPI-30% dextran still had the diffuse band with the molecular weight distribution of 28-100 kDa (lane 8, FIG. 1A) that appeared at the same location as the new band in lane 4 (FIG. 1A). Since the new protein species were observed in both lanes 4 and 8 (FIG. 1A), this indicated that the species were linked by covalent bonding other than disulfide. The slightly larger molecular weight of the bands in the presence of 2-mercaptoethanol was due to the larger hydrodynamic size of the S—S reduced proteins.

SDS-PAGE was also performed with carbohydrate staining using the Periodic Acid-Schiff reagent (PAS) (FIG. 1B). No bands were observed for lanes 1-3 and 5-7. This is because protein bands are not stained by PAS. Being a neutral molecule, dextran could not migrate into the separating gel. Similar to FIG. 1A, a faint high molecular weight band was observed at the top of the gel in lane 4 (FIG. 1B) and it disappeared in lane 8 (FIG. 1B), indicating that the polymers (lane 4) were reduced into small molecules in the presence of 2-mercaptoethanol (lane 8). The same broad diffuse bands as in the lanes 4 and 8 (FIG. 1A) were also observed in the separating gel in lanes 4 and 8 of FIG. 1B, corresponding to a molecular weight distribution of 26-98 kDa (lanes 4, FIG. 1B), and 28-100 kDa (lanes 8, FIG. 1B), respectively. The above results confirmed that glycosylated protein species, such as WPI-dextran conjugates, were formed in the mixture of 10% WPI-30% dextran as a result of heating at 60° C. for 24 h. The molecular weight distribution of the conjugates was 26-98 kDa. Some conjugates were also linked through disulfide bonding of proteins.

The broad molecular weight distribution of the conjugate bands was due to the nature of the components of the two reactants. WPI consists of several protein types, such as α-La (~18%), β-Lg (~52%), BSA and IgG (5%) (Wang and Lucey, 2003, *J. Dairy Sci.* 86: 3091-3101). Each protein contains multiple potential reactive sites. For example, β-Lg contains 16 potential reactive primary amino groups, which are one α-$NH_2$ group at the N-terminal and fifteen ε-$NH_2$ of the lysine residues. From the intensity of the remaining bands of WPI proteins (FIG. 1A), it appeared that each of the WPI proteins was partly involved in the conjugation of WPI-dextran to different extents. The molecular weight of dextran varies from 8,500-11,500 Da as indicated by the supplier (Sigma). The polydispersity of dextran also led to a broad molecular weight distribution of the WPI-dextran conjugates.

Confirmation of Schiff Base Formation in WPI-Dextran Conjugates by DUV

Figure 2:
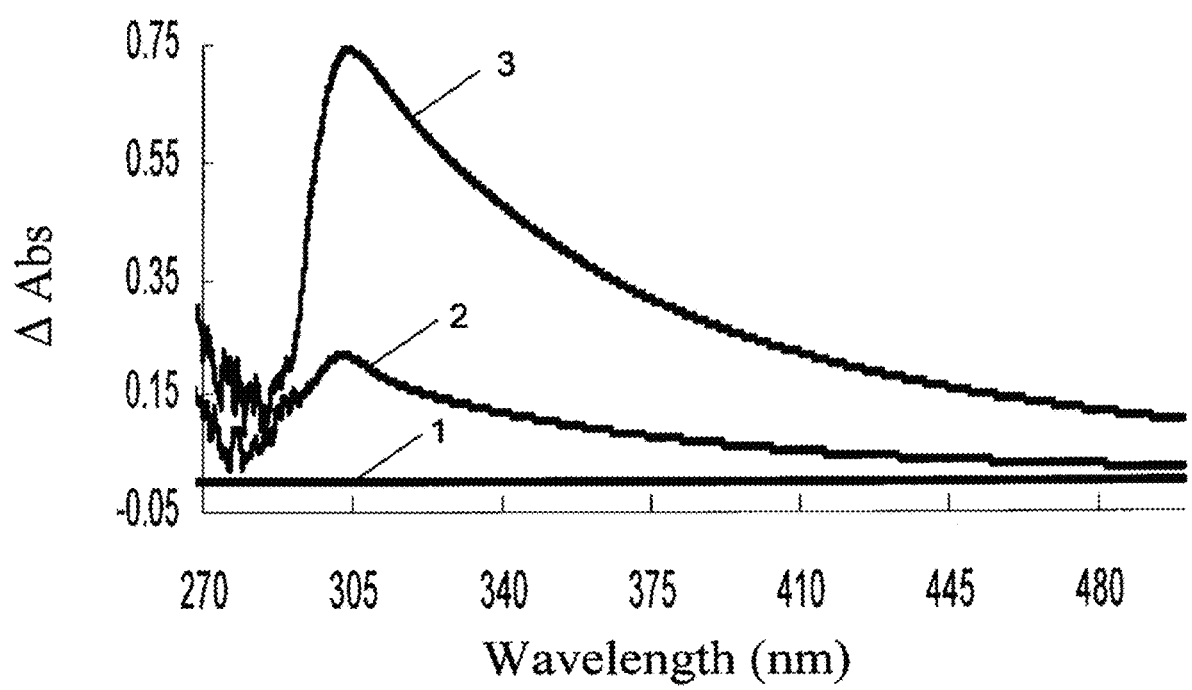
FIG. 2 is a graph showing the difference in UV absorbance spectra (DUV) of Schiff base of WPI-dextran conjugates. Curve 1: 30% dextran (60° C. for 24 h). Curve 2: 10% WPI (60° C. for 24 h). Curve 3: mixture of 10% WPI-30% dextran (60° C. for 24 h).

In order to further clarify the nature of the covalent bonding in WPI-dextran conjugates, DUV spectra were recorded by scanning wavelength between 270-500 nm. As shown in FIG. 2, for the heated mixture of 10% WPI-30% dextran solution, the interaction of WPI-dextran resulted in a DUV spectrum characterized by a maximum at 304 nm, which was a clear indication of Schiff-base formation (Heinert and Martell, 1963, *J. Am. Chem. Soc.* 85: 183-188; Blonski et al., 1997, *Biochem. J.* 323: 71-77). No change in absorbance was observed for a heated 30% dextran solution over all the scanned wavelengths. A small absorbance peak at 304 nm was observed for the heated 10% WPI alone. This was probably caused by some low concentration of residual lactose in WPI (even though it was extensively dialyzed). The DUV measurements shown in FIG. 2 were performed after 33.3-fold dilution of the original samples.

As indicated in FIG. 2, the DUV absorbance peak of the WPI-dextran Schiff base was asymmetric and tailed into the visible wavelengths. This could be explained by the differences in the environment of the Schiff base, which results in a broader absorbance peak. It was also possible that the simultaneous formation of many chromophores led to the tailing of the peak as reported in other studies (Hofmann, 1998, *J. Agric Food Chem.* 46: 3891-3895). The conjugates of WPI-dextran mainly consisted of the Schiff base due to formation of this peak at 304 nm. The DUV absorbance value at 304 nm was used to estimate the extent of the conjugation.

Storage of the Schiff base (without dilution at −80° C. for at least three months; or a diluted, 33.3 fold, solution at 5° C. for at least 1 week) did not result in any change in absorbance value at 304 nm, indicating that the Schiff base of WPI-dextran conjugates was stable. Not wanting to be bound by the following explanation, this stability was probably due to the water restricted environment of the Schiff base C═N bond, thus preventing a $H_2O$ molecule from hydrolyzing the C═N bond.

With prolonged incubation of mixtures of 10% WPI-30% dextran (60° C. for 48 h), the absorbance peak slightly red-shifted to ~310 nm; meanwhile a small new shoulder appeared around 355 nm. The resultant solution was light yellow. This implied that the WPI-dextran conjugates/Schiff base had developed into the intermediate stage of the Maillard reaction.

Time Course of the Conjugation Reaction

Figure 3:
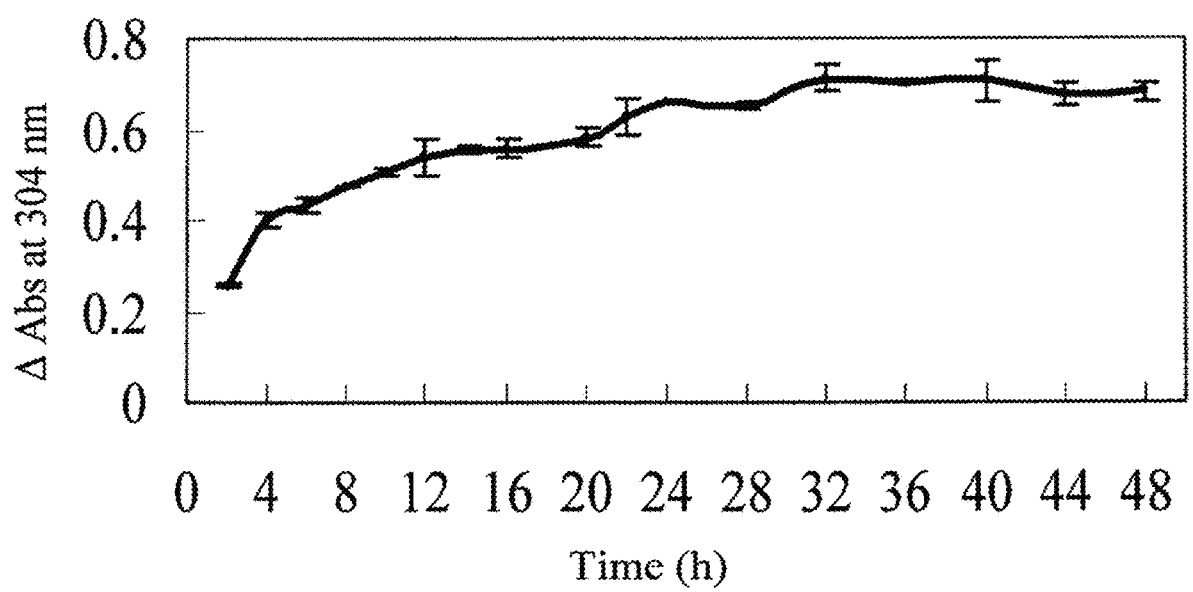
FIG. 3 is a graph showing the time course of WPI-dextran Schiff base formation as indicated by the DUV peak at 304 nm (10% WPI-30% dextran, pH 6.5, 60° C. for 24 h, n=3).

The formation of the Schiff base from a WPI-dextran mixture was studied as a function of time. As shown in FIG. 3, the conjugation reaction was time-dependent. The formation of the conjugates/Schiff base gradually increased with time during the first 24 h when incubated at 60° C. There was little further increase between 24-48 h of incubation at 60° C. (FIG. 3). The measurements shown in FIG. 3 were performed after 33.3-fold dilution of the original samples. SDS-PAGE under reducing conditions and with carbohydrate staining indicated that the molecular weight distribution of the conjugates increased with time from 28-36 kDa (2 h at 60° C.); 28-52 kDa (4 h at 60° C.); 28-70 kDa (6 h at 60° C.); 28-82 kDa (8 h at 60° C.); 28-95 kDa (12 h at 60° C.); and 28-100 kDa (24 h at 60° C.). The intensity of the bands, particularly the lower molecular weight species increased with time. This means that the smaller molecular weight proteins in WPI (α-La, β-Lg) reacted more rapidly with dextran than the large molecular proteins (BSA, IgG), and it was in the order α-La>β-Lg>BSA and IgG. This observation was in agreement with the results of Nacka et al., 1998, *J. Protein Chem.* 17: 495-503, who reported that the glycosylation with reducing sugars with α-La was faster than with β-Lg, based on SDS-PAGE. The higher concentration of α-La and β-Lg in WPI compared to BSA and IgG was also responsible for the faster conjugation rate of α-La and β-Lg with dextran.

A reaction time of 24 h at 60° C. was chosen under the experimental conditions to allow the reaction to proceed with the highest yield of Schiff base but with low levels of intermediate and advanced Maillard products.

Effect of WPI and Dextran Concentration on Schiff Base Formation

Figure 4:
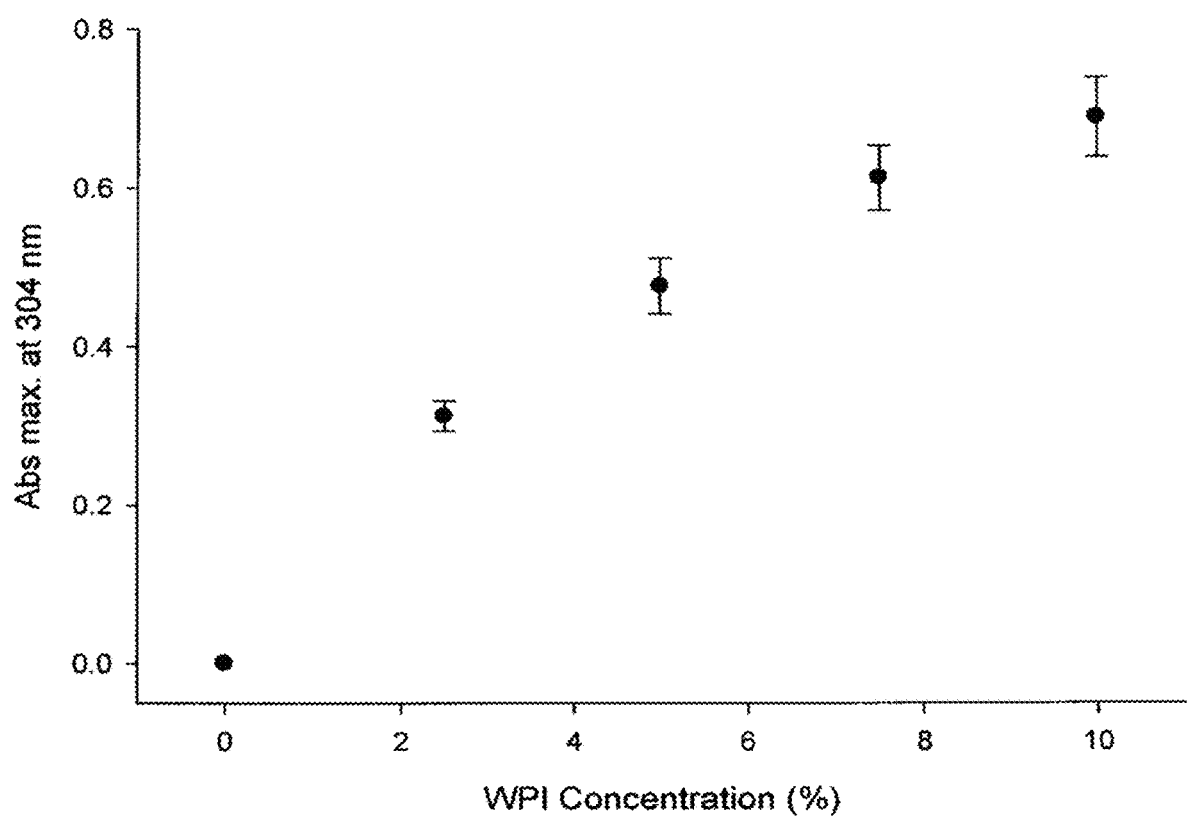
FIG. 4 is a graph showing the effect of WPI concentration on the WPI-dextran Schiff base formation (30% dextran, pH 6.5, 60° C. for 24 h, n=3).

The effect of WPI or dextran concentration on the conjugation of WPI-dextran was examined. As shown in FIG. 4, the formation of WPI-dextran Schiff base increased almost linearly with increasing WPI concentration from 2.5 to 10% in a mixture with 30% dextran. Further increases in the WPI concentration above 10% led to the gelation of WPI during heating at 60° C. Each protein in WPI has multiple potential reactive amine groups. However, at pH 6.5, most of the ε-amino groups (>99%) are in the protonated form, which are not reactive. The measurements shown in FIG. 4 were performed after 33.3-fold dilution of the original samples.

Figure 5:
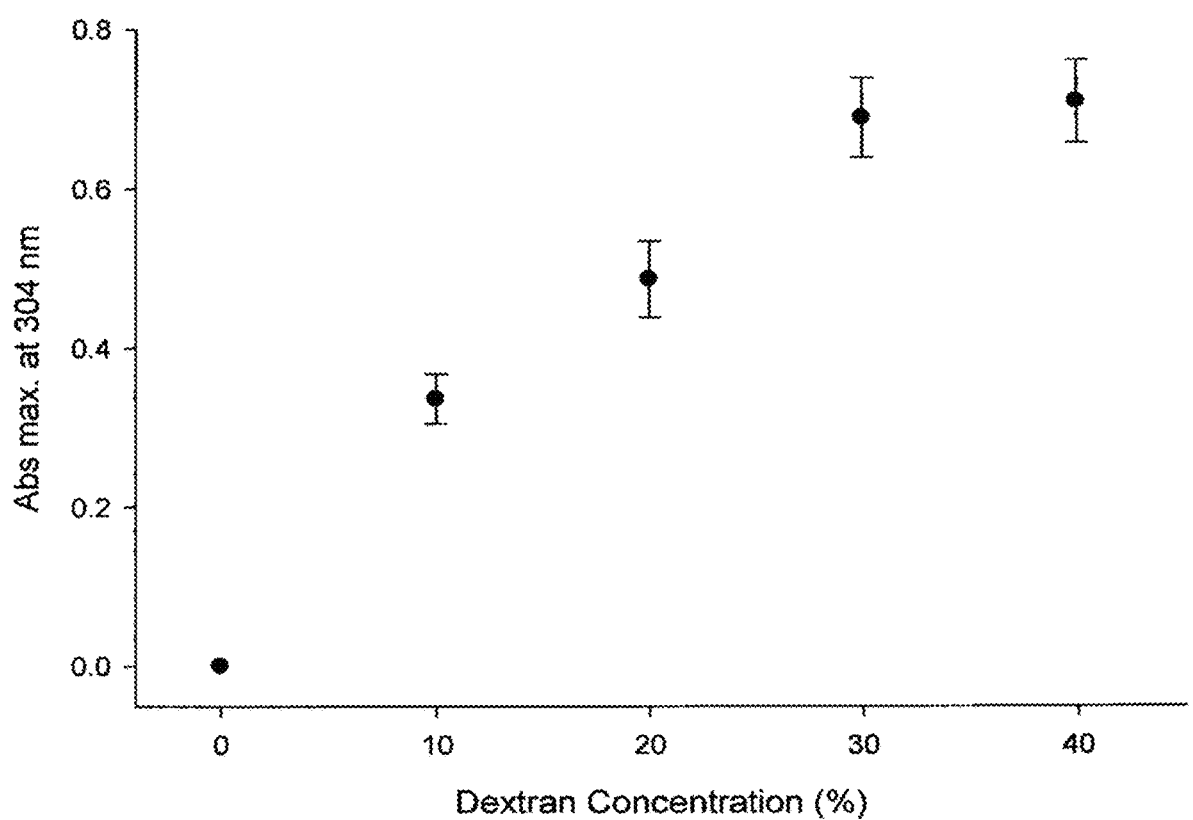
FIG. 5 is a graph showing the effect of dextran concentration on the WPI-dextran Schiff base formation (10% WPI, pH 6.5, 60° C. for 24 h, n=3).

The effective concentration of —$NH_2$ groups in the system is lower than the concentration of carbonyl group. Therefore, the conjugation increases almost linearly with WPI concentration. In FIG. 5, the formation of WPI-dextran Schiff base increased with the increase in dextran concentration from 10 to 40%, in mixtures with 10% WPI. The measurements shown in FIG. 5 were performed after 33.3-fold dilution of the original samples. Dickinson and Semenova (1992, *Colloids Surf* 64: 299-310) thought that each polysaccharide molecule (dextran) has only one reducing group capable of reacting with amine groups in proteins, and thus the extent of conjugate formation increases with an increase in the proportion of polysaccharide. This is also true for protein amino groups at pH 6.5 since more than 99% of the amino groups are in the non-reactive $NH_3^+$ form. The fitting-equation in FIG. 5 indicated that the conjugation degree was positively related to the logarithm of the concentration of dextran. This might be related to the bulk structure of dextran that restricts its access to the reactive sites of the amino groups on proteins.

Increasing the dextran concentration from 30 to 40% did not result in significant increase in the WPI-dextran Schiff base formation (FIG. 5), but a marked increase in viscosity was observed. It is possible that the high viscosity prevented the accessibility of the reducing end of dextran to WPI proteins due to the overlapping and interpenetration of the coil structure of dextran molecules with themselves at very high concentrations; 10% WPI and 30% dextran were therefore chosen for the conjugate formation.

An excess of polysaccharide compared to protein in the mixture of reactants (1:3-1:9, by weight) is often used in preparing Maillard reaction products by dry-heating. There is a lack of detailed explanation for this ratio. One plausible explanation was that each polysaccharide molecule has only one reducing group capable of reacting with amine groups in the proteins, thus the extent of conjugate formation would increase with increasing proportion of polysaccharide (Dickinson and Semenova, 1992, *Colloids Surf* 64: 299-310). However, for the reaction in aqueous solutions, the mixing ratio of reactants did not mean it was the binding ratio of protein to polysaccharides. For the conjugates formed at 10% WPI-30% dextran (pH 6.5, 60° C. for 24 h), the compositional analysis of the individual components indicated that only 1.9% (by weight) WPI and 5.6% (by weight) dextran were involved in the formation of WPI-dextran Schiff base. Most dextran molecules remained unreacted. Not wanting to be bound by the following explanation, this could be the consequence of a crowding effect, due to the high dextran concentration in the mixture of 10% WPI-30% dextran, that led to an increased probability of collisions between amino groups on WPI proteins and carbonyl groups on dextran, thus promoting the conjugation reaction (Ralston, 1990, *J. Chem. Educ.* 67: 857-860; Minton, 1997, *Curr. Opin. Biotech.* 8: 65-69; Somalinga and Roy, 2002, *J. Biol. Chem.* 227: 43253-43261). The association of WPI, which might be also enhanced by crowding effect, was offset by the protective effect of dextran, as discussed previously.

Effect of Temperature and pH

Figure 6:
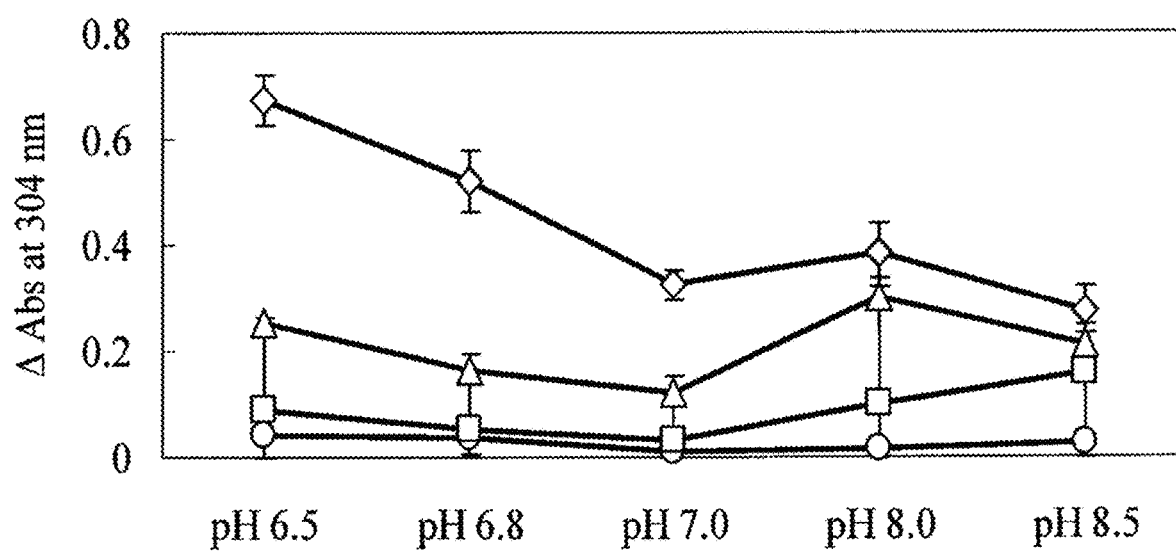
FIG. 6 is a graph showing the effect of temperature [40° C. (○); 50° C. (□); 56° C. (Δ); 60° C. (◇)] and pH on the WPI-dextran Schiff base formation (10% WPI-30% dextran, 60° C. for 24 h, n=3).

Heating a mixture of WPI and dextran solution promotes two competitive reactions—aggregation of WPI proteins and conjugation between WPI and dextran. High temperature favors the conjugation reaction, as chemical reactions are favored by an increase in temperature. High temperature also promotes WPI denaturation/aggregation, thus leading to the loss of reactant for the conjugation of WPI-dextran. The critical structural changes in β-lg occur at 63° C. and pH 7.0 (from circular dichroism spectroscopy; Prabakaran and Damodaran, 1997, *J. Agric. Food Chem.* 45: 4303-4308); the denaturation temperatures of α-La is 64° C. at pH 7.0 (from differential scanning calorimetry; McGuffey et al., 2005, *J. Agric. Food Chem.* 53: 3182-3190); and BSA is 62.2° C. at pH 6.7 (Mulvihill and Donovan, 1987, *J. Food Sci. Tech.* 11: 43-75). Therefore, the effect of temperature on the conjugation of WPI-dextran was investigated at <60° C. in order to minimize denaturation/aggregation of WPI proteins. Dextran is stable at ambient temperatures over the range of pH 4-10. Any structural change in dextran during heat processing was ignored in this study. As shown in FIG. 6, the Schiff base was hardly formed at low temperatures (40 or 50° C.) over the pH range studied. Regardless of pH, the formation of Schiff base was favored by raising the temperature.

As far as pH was concerned, as seen in FIG. 6, the effect of pH on the Schiff base formation was negligible at lower temperatures (40° C. and 50° C.). At 60° C., the formation of Schiff base was significantly enhanced by reducing the pH from 7.0 to 6.5. There was no significant difference in the reaction in the pH range 7.0 to 8.5. The generation of Schiff base was greatly enhanced at pH 6.5. This was in good agreement with the literature (Ames, 1990, *Trends Food Sci. Tech.* 1: 150-154). In one example, the conditions pH 6.5 and 60° C. were used to maximize the extent of formation of Schiff base in the study. The measurements shown in FIG. 6 were performed after 33.3-fold dilution of the original samples.

Effect of Hydrostatic Pressure on the Schiff Base Formation

To examine if the formation of WPI-dextran conjugate/Schiff base would be facilitated by applying elevated pressure, hydrostatic pressure (7.9 MPa) was used in combination with heating during incubation. For the WPI proteins, the pressure required to unfold the proteins has been reported to be 50, 200 and 800 MPa for β-Lg, α-La and BSA, respectively (López-Fandiño, 2006, *Crit. Rev. Food Sci. Nutr.* 46: 351-363). Considering the protective effect of polysaccharides on proteins against elevated pressure (Galazka et al., 1999, *Food Hydrocoll.* 13: 81-88), the conformational change of WPI proteins under 7.9 MPa pressure could be neglected. Assuming that the structure of dextran was not affected by the applied pressure, any pressure-induced difference was assumed to be due to an impact on the conjugation reaction.

Figure 7:
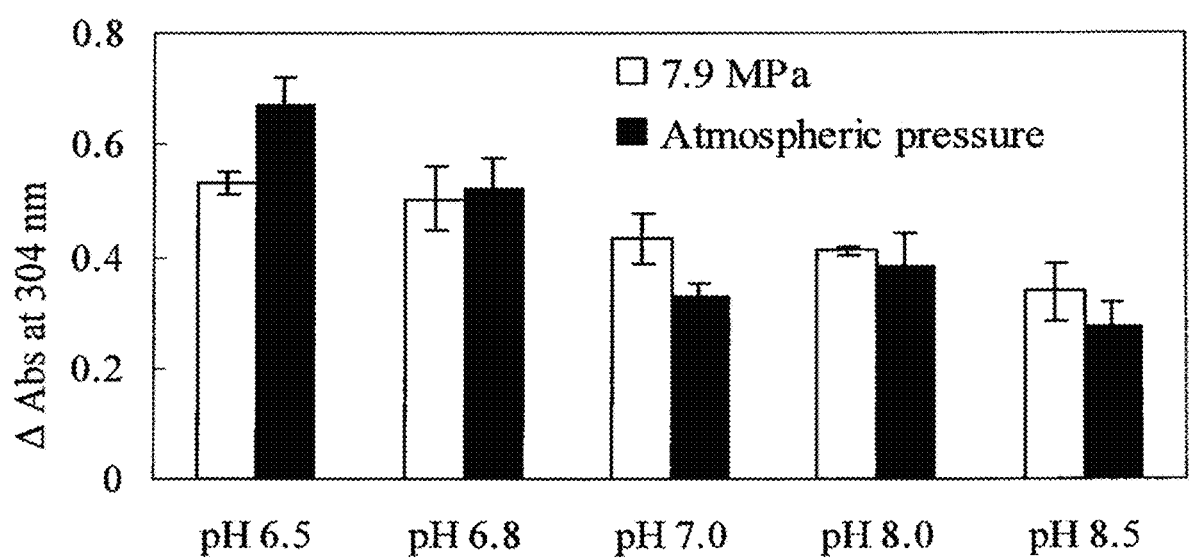
FIG. 7 is a graph showing the effect of hydrostatic pressure on the WPI-dextran Schiff base formation at various pH values (10% WPI-30% dextran, 60° C. for 24 h, n=3).

As shown in FIG. 7, the amount of Schiff base at 7.9 MPa was marginally increased by reducing the pH from 8.5 to 8.0 compared with the reaction at atmospheric pressure. Schiff base formation was significantly inhibited by the application of pressure at pH 6.5, but significantly enhanced at pH 7.0 compared to at atmospheric pressure. The lack of influence of pressure could be due to the low pressures used in this study.

There have been various reports about the impact of pressure on the initial step of the Maillard reaction. For example, high pressure (50-500 MPa, 50° C., pH 8.2) hardly affected the initial condensation reactions (Tamaoka et al., 1991, *Agric. Biol. Chem.* 55: 2071-2074). However, high pressure (60 MPa, at 70° C.) was reported to accelerate the initial reactions at pH 7.0 due to the negative activation volume (Isaacs and Coulson, 1996, *J. Phys. Org. Chem.* 9: 639-644). These observations were in accordance with the results herein; that is, the effect of pressure was related to the pH of solution. Moreover, Moreno et al., 2003, *J. Agric. Food Chem.* 51: 394-400) reported that at 400 MPa (60° C., pH 5-8) Amadori rearrangement products were not appreciably affected by pressure in unbuffered media but were suppressed in buffered media. It was attributed to the pressure-induced dissociation of the acid groups. It was possible that, due to the pressure-induced dissociation of the acid groups, high pressure accelerated the condensation reaction of ε-amino to carbonyl at pH≥7.0; but it retarded the formation of the adduct due to the protonation of the ε-amino group at pH<7.0.

Emulsifying Properties of Protein-Polysaccharide Conjugates

In general, PPC exhibit better functional properties than proteins and PS alone. It is likely (but not certain) that this improvement can be attributed to the structure and size of the conjugate (Chevalier et al., 2001, *Int Dairy J.* 11: 145-152). Thus, the functional properties of PPC are of interest especially for their viscosity, gelation and emulsifying abilities. For example, a superior biopolymer for use in oil-in-water emulsions would be a PPC that combines the surface-active properties of the protein with the potential steric-stabilizing properties of the associated PS (Dickinson and Semenova, 1992, *Colloids Surf* 64: 299-310). The hydrophilic nature of the PS should allow it to extend into the aqueous phase.

Figure 8:
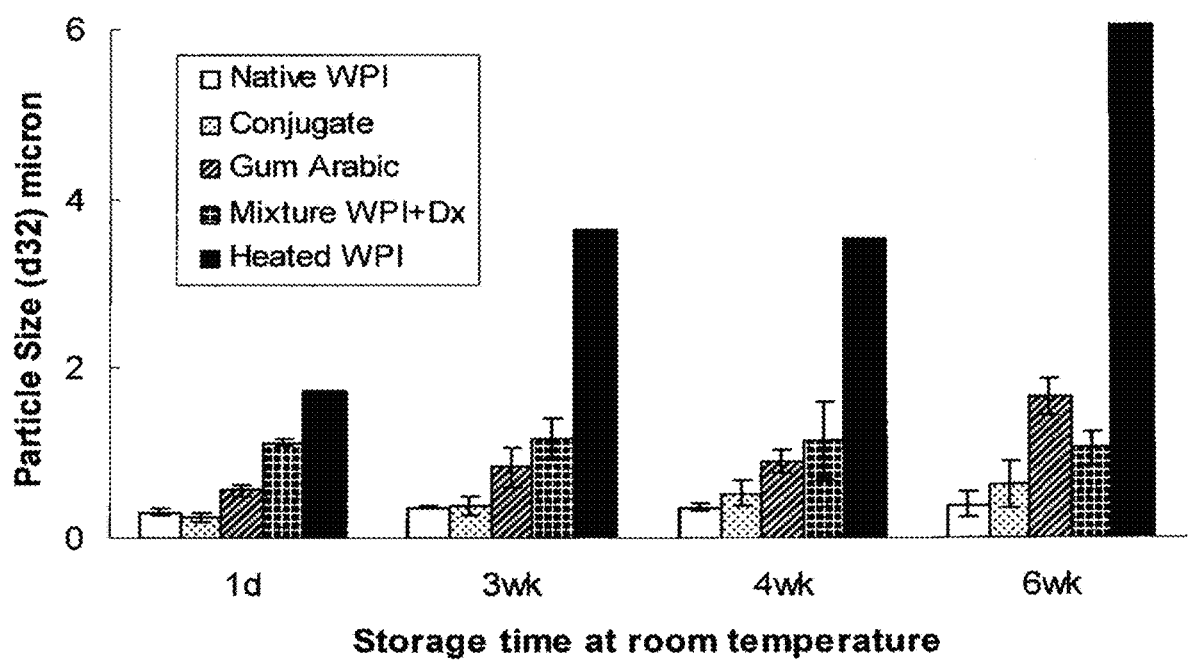
FIG. 8 is a graph illustrating the emulsifying properties of protein-polysaccharide conjugates produced according to the present invention.

In one example, preparation of emulsions from purified PPC prepared from the conjugation of WPI with dextran (500 kDa). FIG. 8 shows particle size distribution (d32) of emulsions during storage that were prepared with 0.5% (wt) of each emulsifying material, 20% (v/v) soybean oil, 10 mM NaPi buffer, pH 6.5, 0.02% $NaN_3$. Emulsions were prepared with an Avestin EmulsiFlex high pressure homogenizer (1.5 kilobar). Samples were stored at room temperature for at least 6 weeks. The performance of the PPC made in accordance with the present invention was compared with gum arabic as well as WPI and mixtures of WPI and dextran, Dx. The produced PPC contains about 10% protein, i.e. 0.05% protein for the PPC sample. All emulsions were stabilized with 0.5% (wt/wt) of emulsifying material. Even with the low level of protein the novel emulsions stabilized with PPC were not significantly different from those stabilized with 0.5% WPI. This indicated that the produced PPC was an excellent emulsifier and superior to gum arabic. Simple mixtures of WPI with dextran (not conjugated) did not produce stable emulsions since the protein level was very low (0.05%) in these samples.

Solubility of the Protein-Polysaccharide Conjugates

Figure 9:
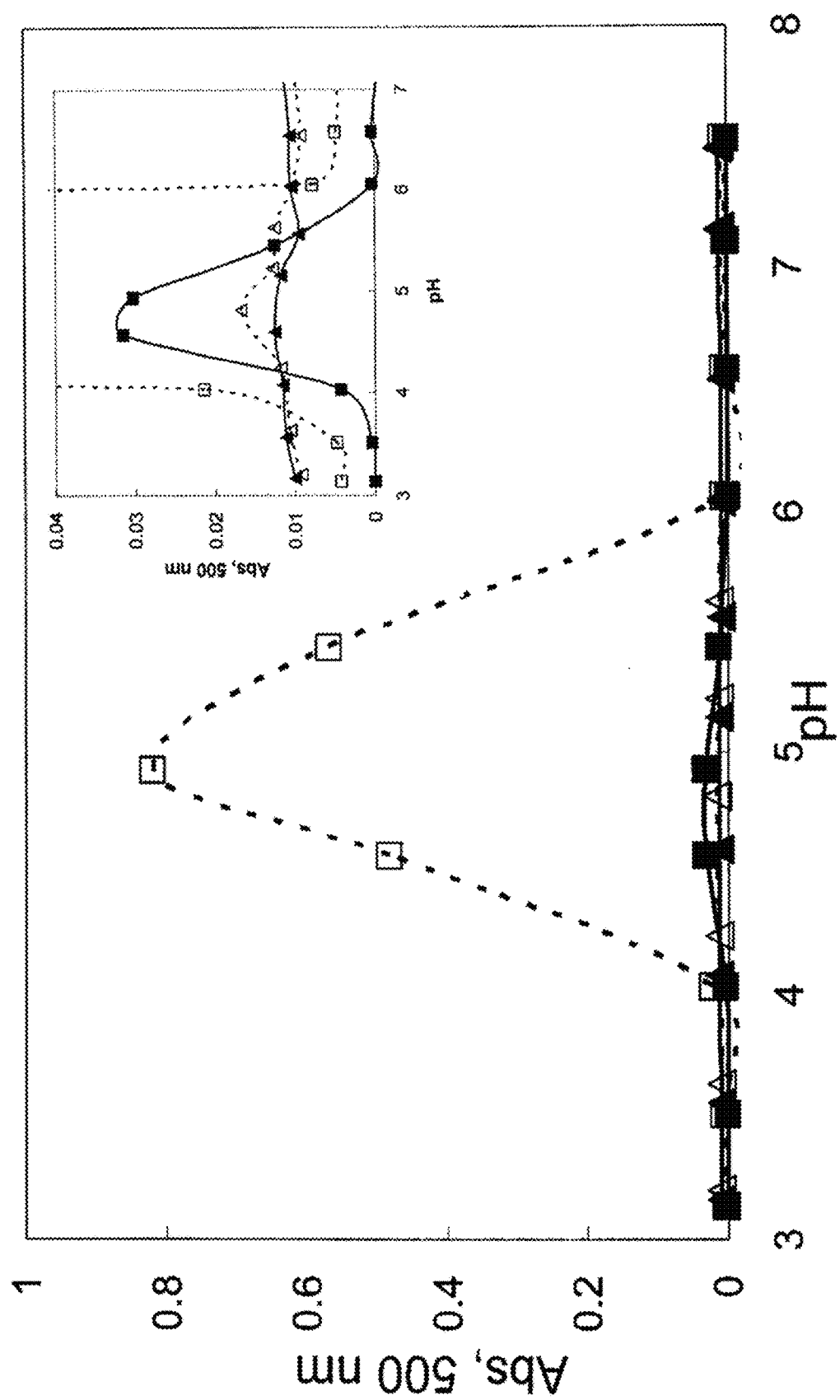
FIG. 9 is a graph showing the solubility of conjugates (0.1% protein) at room temperature and heated 30 min at 80° C. within the pH range 3.5-7.5, in comparison with whey protein (0.1% WPI). The higher the absorbance at 500 nm, the lower the solubility is.

FIG. 9 is a graph showing the solubility of conjugates (0.1% protein) at room temperature and heated 30 min at 80° C. within the pH range 3.5-7.5, in comparison with whey protein (0.1% WPI). The higher the absorbance at 500 nm, the lower the solubility is.

Figure 10:
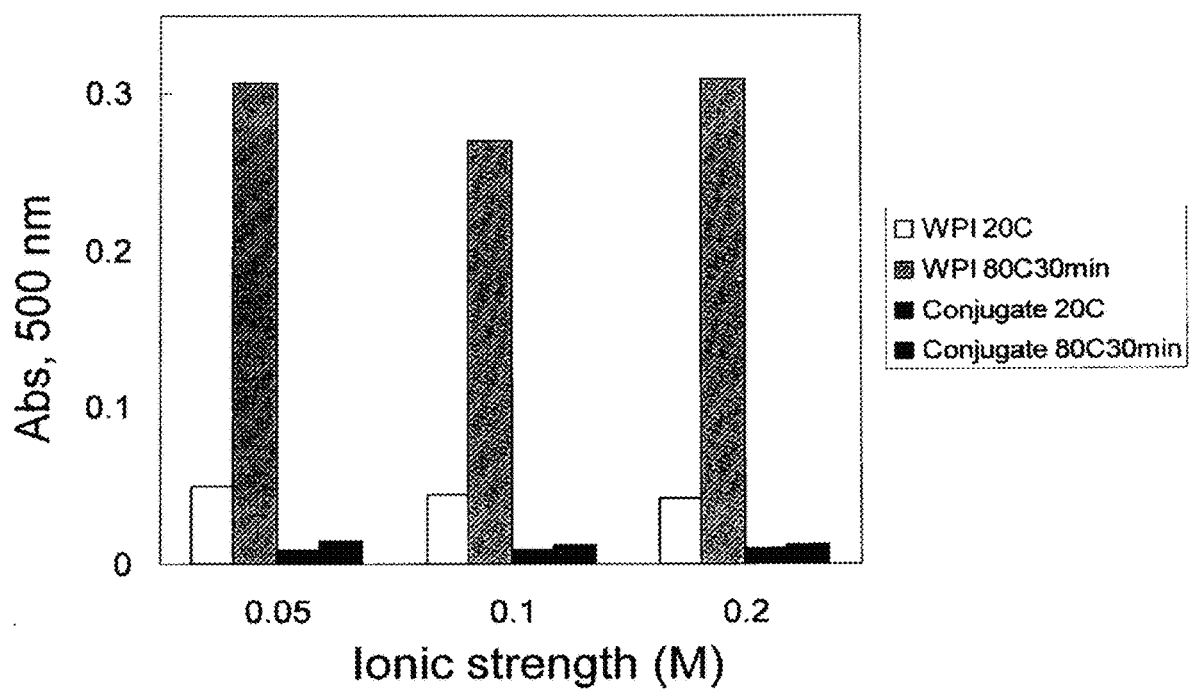
FIG. 10 is a graph showing the solubility of conjugates (0.1% protein, pH 4.5) at room temperature and heated 30 min at 80° C., in comparison with whey protein (0.1% WPI). The higher the absorbance at 500 nm, the lower the solubility is.

FIG. 10 is a graph showing the solubility of conjugates (0.1% protein, pH 4.5) at room temperature and heated 30 min at 80° C., in comparison with whey protein (0.1% WPI). The higher the absorbance at 500 nm, the lower the solubility is.

Thermal Stability of the Protein-Polysaccharide Conjugates

Figure 11:
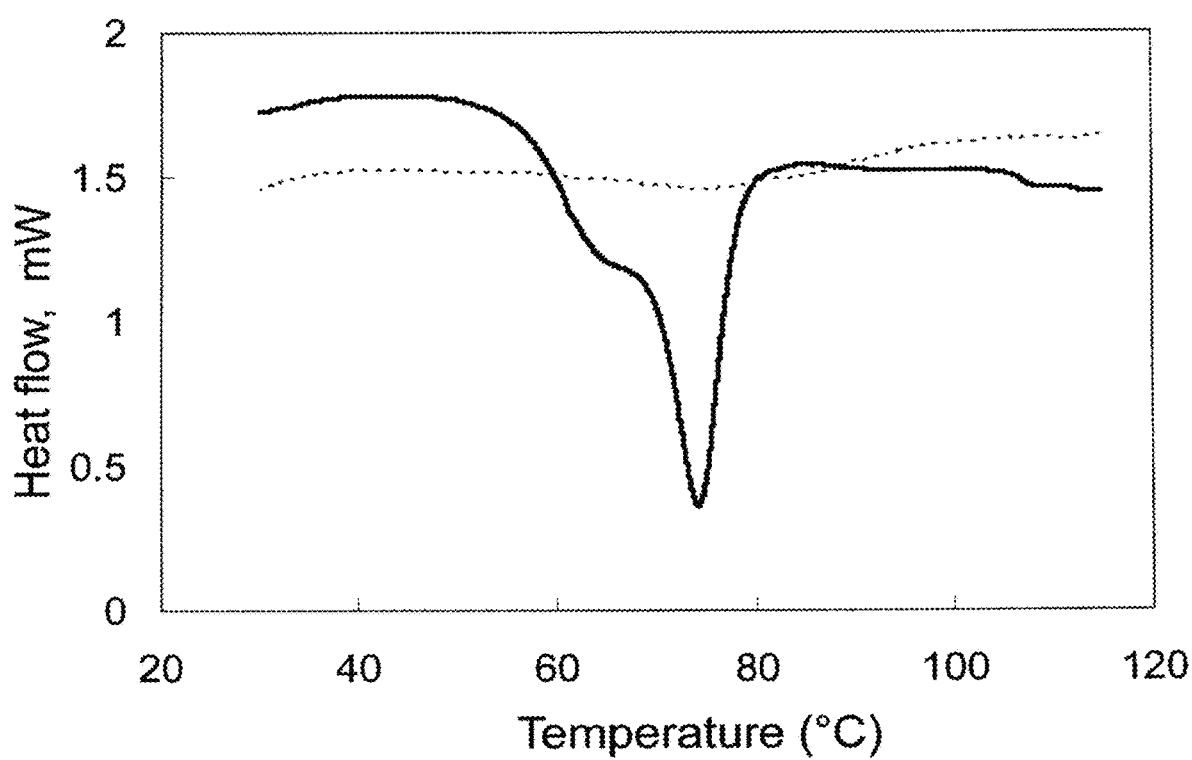
FIG. 11 is a graph showing thermal stability of the conjugate, as a DSC heating scan (1.0° C./min) for 10% conjugate (dotted line) and 10% WPI (solid line) at pH 8.5.

FIG. 11 is a graph showing thermal stability of the obtained conjugates. A DSC heating scan (1.0° C./min) for 10% conjugate (dotted line) and 10% WPI (solid line) at pH 8.5 is shown. The conjugates had greatly improved thermal stability.

Effect of Solids Content of a Mixture of Sodium Caseinate

Figure 12:
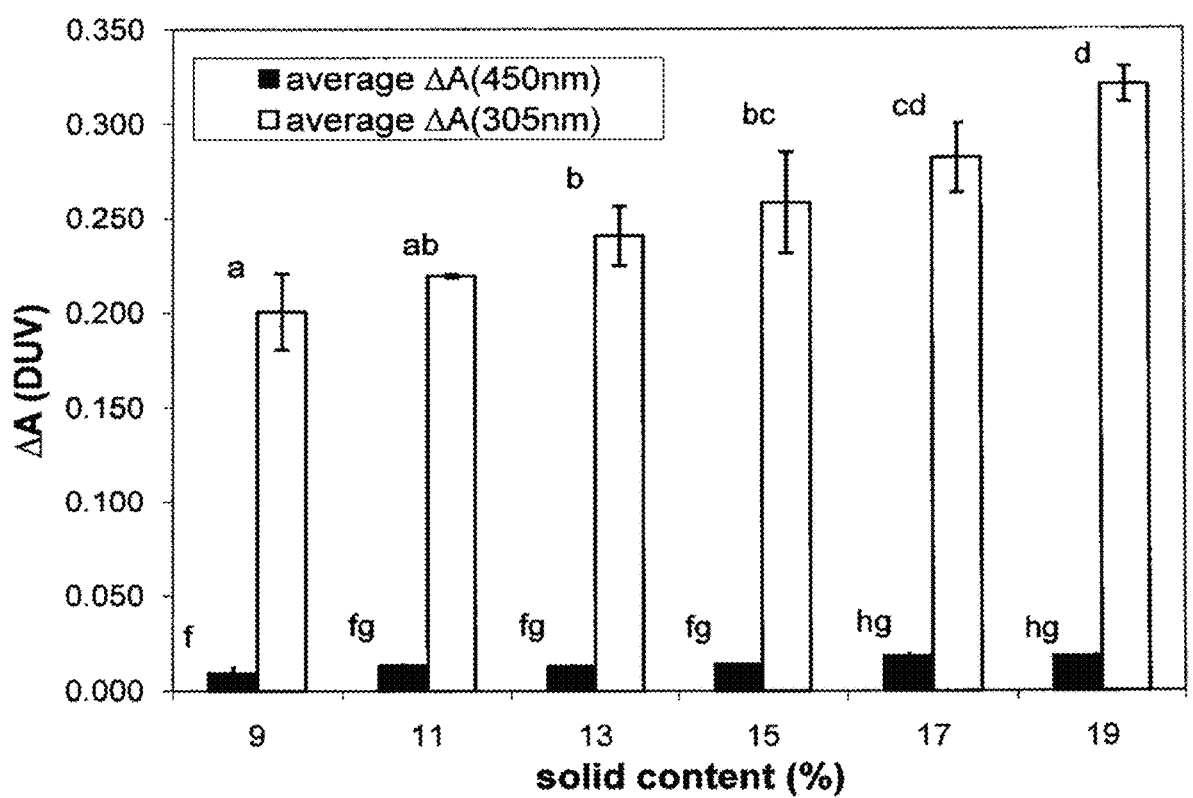
FIG. 12 is a graph showing the effect of solids content of a mixture of sodium caseinate: maltodextrin (1:1 ratio) on the formation of Schiff base, as indicated by the ΔA305 nm or change in difference UV spectroscopy (DUV) at 305 nm and color (ΔA450 nm).

FIG. 12 is a graph showing the effect of solids content of a mixture of sodium caseinate: maltodextrin (1:1 ratio) on the formation of Schiff base (as indicated by the AA305 nm or change in DUV at 305 nm) and color (AA450 nm). Samples were heated for 90 min at 95° C. and pH 6.5 Maltodextrin was 250 DE. Different letters indicate significant differences (P<0.05). This demonstrates that other types of proteins and polysaccharides (apart from, or in addition to, whey protein and dextran) can successfully undergo this reaction.

Measurement of Emulsion Stability by Whey Protein-Dextran Conjugates and the Stability of Emulsions After Heat Treatment and in Low pH/High Salt Systems Radiolabeling of Protein-Polysaccharide Conjugate. The conjugate is radiolabeled with [$^{14}C$] nuclide by reductive methylation of amino groups with [$^{14}C$]-formaldehyde. Briefly, 60 µl of [$^{14}C$]-formaldehyde solution (containing 0.01 mmol of formaldehyde (having a total radioactivity of 0.1 mCi) is mixed with 40 ml of 20 mM phosphate buffer containing 40 mg of protein, followed by addition of 50 mg of $NaCNBH_3$. After incubation for 2 h at room temperature, the reaction mixture is dialyzed exhaustively against pure water (surface tension 72.9 dynes/cm at 20° C.) and lyophilized in cryo-vials and stored frozen at −70° C. This labeling protocol usually results in [$^{14}$C] labeling of about 1-2 amino group per protein molecule.

Adsorption at the oil-water interface. Adsorption of PPC from the aqueous phase to the triolein-water interface is studied by the surface radiotracer method. A brief description of this method is as follows. The method essentially involves spreading of a 100 nm thick triolein layer on water surface and monitoring adsorption of $^{14}$C-radiolabeled proteins using a surface radiotracer probe. The surface tension is measured by the Wilhelmy plate technique using a ST 9000 surface Tensiometer (Nima Technology Ltd., Coventry, England), interfaced with an IBM PC. The apparatus consists of teflon trough having inner dimensions of 17.45× 5.5×4 cm$^3$. One side of the trough has a small hole (1 mm diameter) capped tightly with a septum for injecting the protein solution into the bulk phase. In each experiment, 350 mL of a solution consisting of 20 mM phosphate buffer (pH 7.0) adjusted to 0.1 M ionic strength with NaCl is used as the bulk phase. Prior to spreading the triolein film over the buffer surface, a very thin (3 mm dia, 12.7 mm length). Teflon-coated magnetic stir bar is placed at the center of the trough and the radiotracer probe (Ludlum Measurements, Inc., Sweetwater, Tex.) and the Wilhelmy plate is placed in position. The method for spreading a 1000 nm thick triolein film has been described in detail elsewhere (Sengupta and Damodaran, 1998, *J. Colloid Interface Sci.* 206: 407-415).

To initiate protein adsorption, a known volume (0.5-2.0 ml) of the radio-labeled protein/PPC stock solution is injected through the septum on the side of the trough. The final concentration of protein in the bulk solution is in the range of 1-10 μg mL$^{-1}$ ($10^{-4}$-$10^{-3}$% w/v). The surface tension and surface radioactivity (cpm) measurements are initiated soon after injecting the protein solution. The bulk phase is stirred gently by using the stir bar at low speed (60 rpm), which does not cause ripples on the triolein film. The bulk phase is stirred only for the first 15 minutes.

The surface tension and surface cpm is continuously monitored until they reach an equilibrium value, which usually takes about 20-24 h. In these experiments, the attainment of equilibrium is defined as the condition when the surface cpm does not change for at least 4 h. The cpm is recorded using a rate meter (Model 2200, Ludlum Measurements, Sweetwater, Tex.) and printed out on a strip chart recorder interfaced with the rate meter. The cpm measurements are made at 1 min intervals for the first hour of the experiment, followed by measurements at 10 min intervals thereafter. Calibration curves required for converting cpm readings at the oil-water interface into interfacial protein concentrations (mg m$^{-2}$) are constructed as described elsewhere (Sengupta and Damodaran, 1998, *J. Colloid Interface Sci.* 206: 407-415).

The cpm versus interfacial radioactivity (μCi m$^{-2}$) calibration curve is constructed by spreading $^{14}$C-labeled β-casein at the oil-water interface. The cpm arising from radioactivity of protein in the bulk solution is determined from a standard curve relating interfacial cpm versus bulk radioactivity of Na$_2$$^{14}$CO$_3$. The interfacial radioactivity (μCi m$^{-2}$) is determined by dividing the background-corrected cpm with the slope of the cpm versus interfacial radioactivity calibration curve. The interfacial protein concentration (mg m$^{-2}$) is obtained by dividing the instantaneous interfacial radioactivity (μCi m$^{-2}$) with the specific radioactivity of the protein (μCi mg$^{-1}$).

Experiments may be conducted on both native protein and PPC to elucidate the effect of the PS moiety on the rate and extent of adsorption as well as on the final surface tension values.

Emulsifying Properties. To develop a basic understanding of the effect of the PS moiety on interfacial properties of proteins, the emulsifying properties of PPC conjugates are examined and compared to pure proteins. Emulsions may be prepared by homogenizing 1% protein or PPC solutions in 20 mM imidazole-HCl buffer, pH 7.0, containing 0.02% sodium azide, with soybean oil. The volume fraction of oil in all emulsions is set at 20% v/v. A coarse emulsion of the protein solution and oil mixture is homogenized (two passes) in an Emulsiflex-B3 (Avestin Inc., Ontario, Canada) homogenizer at an input pressure of 200 kPa, corresponding to a pressure drop of 40 MPa. This provides an emulsion with about 1 μm average particle size distribution. The kinetic stability of the emulsion over a period of 30 days at 25° C. is studied by measuring rate of change of emulsion droplet size using the Malvern Mastersizer. Specifically, changes in the size distribution and total interfacial area of the emulsion as a function of storage time is determined for emulsions made with PPC and pure proteins. The impact of processing conditions is tested, including various heat treatments, salts and pH values on the properties of the obtained PPC-stabilized emulsions and these are compared to WPI stabilized emulsions.

Measurement of the Astringency of Low pH Beverages Made with Whey Protein-Dextran Conjugates Astringency in protein or PPC fortified beverages is determined using trained sensory panels. Tannic acid solutions at 0, 0.38, 0.60, 0.93, 1.45, and 2.26 mM are used as astringency standard solutions correlating with astringency scores of 0, 2, 4, 6, 8, and 10, respectively. The astringency of the protein sample is evaluated by astringency score compared with the astringency of standard tannic acid solutions. A 10 or 15-point scale is used for the sensory panel (Beecher et al., 2006). Panelists are pre-screened for their ability to correctly detect astringency and differentiate it from other attributes, such as bitterness or sourness. The rate of build-up of astringency during sample evaluation is determined. When the beverage is formulated, one may add enough PPC to achieve between 3 to 5% protein addition. The beverage is adjusted to pH values between 3 to 4.5 and a neutral pH beverage is also examined. 2.0 M HCl or NaOH is used for pH adjustment (Sano et al., 2005, *J. Dairy Sci.* 88: 2312-2317). Protein fortified beverages are dialyzed against 5 mM sodium phosphate buffer, already at the desired pH (to have a similar ionic strength in the beverages). Beverages are either unheated or heated at 85° C. for 10 min. A control beverage is also prepared with unmodified protein (we will use several different commercial brands of WPI). All the beverages are adjusted to the same viscosities (or flow behavior) using added gums. A skilled artisan will know to check that the gums themselves do not alter the astringency of beverages.

The impact of the degree of conjugation and the molecular weight of the PS used for conjugation on the astringency of beverages may be examined. It is possible that there is a minimum molecular weight of dextran that is able to confer the ability to reduce the astringency reaction. The impact of the concentration of added PPC on the astringency of beverages may also be tested. Compared to unmodified whey protein, it may be possible to add a higher concentration of the PPC before exceeding an acceptable astringency threshold (as determined from sensory panelists). Alternatively, one may instead switch to the use of maltodextrin as the PS. In some embodiments, it is possible to conjugate whey proteins with this PS using the methods of the present invention. In addition, one may directly examine the interactions between SPRPs and the PPC of the present invention using the turbidity method of Home et al., 2002, *Chem. Senses* 27: 653-659. The PPC of the present invention may have greatly reduced turbidity compared to the native protein even added at the same concentration.

Conjugation of Whey Proteins or Whey Protein Hydrolysates May Reduce Milk Allergenicity WPI, pure β-Lg (Sigma), and whey proteins hydrolyzed to various extents (DH values) may be conjugated in these experiments. Before use, WPI, β-Ig and whey hydrolyzates are dissolved in Milli-Q water and thoroughly dialyzed against Milli-Q water (dialysis membrane tubing molecular weight cut-off 6,000-8,000 Da) to remove free lactose for 3 days at 5° C. with changes in water every 6 hours. After lyophilization, purified proteins are stored at 5° C. for use. Commercial infant formula that contains partially hydrolyzed whey, e.g. Good Start Milk Based Infant Formula Powder (Nestle), also may be used.

The impact of the molecular weight of PS (10-500 kDa) on allergenicity may be examined. Various methods for detecting milk allergens exist. In vitro tests that measure the capacity of specific IgE from serum of allergic patients to bind the modified protein(s) may be used. Sera of a number (e.g. at least 20) patients with a history of reactions to cow's milk are obtained. Approximately 10 ml is obtained from these patients for allergenicity testing. Serum of a subject without CMA is used as a control. Allergenicity is determined using specific ELISA immunoassays for whey proteins (commercially available, e.g. Neogen and R-Biopharm) and allergen specific IgE methods such as Western blotting and RAST (Hamilton and Adkinson, 1983; *J. Clinical Immunoassay* 6: 147-153). Purified PPC is used as the allergen in IgE enzyme-linked immunosorbent assay (ELISA). Most ELISAs are not successful in the analysis of hydrolyzed protein, thus allergenicity may also be checked via IgE methods such as Western blotting and radioallergosorbent test (RAST).

An example of the general test method for a commercial ELISA test for milk allergens from Neogen is as follows: ELISA microtiter plates (100 μl/well) are used. PPC conjugate (various concentrations, e.g. 1-10 μg/ml) is added to antibody-coated wells (capture antibody). Unbound residue is washed away and a second, enzyme-labeled antibody (detector antibody) is added. The detector antibody binds to the already bound PPC. After a second wash, the substrate is added (e.g. 100 μl of patient or control serum, diluted 1:10). Color develops as a result of the presence of bound detector antibody. Red Stop reagent is added and the color of the resulting solution is observed. A microwell ELISA reader is used to yield optical densities. Control optical densities form a standard curve, and sample optical densities are plotted against the curve to calculate the concentration of PPC.

Various types of commercially available kits may be used. Alternatively, methods similar to the one described by Hattori et al., 2004, *J. Agricultural and Food Chemistry* 52, 4546-4553, may be used. Alternatively, it may be possible to test the conjugate prepared from purified β-Lg. PPC may reduce the antigenicity of β-Lg and whey proteins. The reduction in the antigenicity of β-Lg by conjugation may depend on the molecular weight of the PS as large PS could shield epitopes.

A Western blotting technique similar to that reported by Matheu et al., 2004, *Clinical and Molecular Allergy* 2: 2, is used. SDS-PAGE is performed with a 12% polyacrylamide gel and a stacking gel of 4% (this is varied depending on the molecular weight of the PPC). About 5-20 μg of purified PPC are applied to every lane and electrophoresis is performed (Mini Protean II System, Bio-Rad laboratories, Richmond, USA). Then, proteins are electrophoretically transferred from the separating gel to Immobilon-P™ (PVDF, Millipore Corporation, Billerica, Mass., USA) membranes in a transfer buffer. After blocking with a solution of gelatin 3% for 1 hour, the membranes are washed and incubated overnight with patient's and normal control sera. Next day, membranes are washed and incubated with goat anti-human IgE-labelled-peroxidase. Detection is performed with a chemiluminescence substrate (Pierce Chemical Company, Rockford, Ill.). The Western-blot should demonstrate if IgE in the CMA patient's serum is bound to some medium/high-molecular weight PPC bands. Control sera should be negative.

The allergenicity of each single protein is due to a number of molecular immunoreactive structures, i.e. the IgE-binding epitopes that are widespread within the protein molecule. The conjugation of whey proteins with dextran molecules may interfere with the IgE-binding epitopes on the protein molecule. In some embodiments, intact β-Ig or WPI may be used in reducing protein allergenicity. Alternatively, partially hydrolyzed whey proteins may be used as this product is only successful with some but not all patients with CMA; thus the conjugation of partially hydrolyzed whey may improve its hypoallergenicity. It is expected that RAST analysis will indicate that IgE reactivity to the PPC of the present invention is at least several fold lower than that of the unmodified protein.

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of chemistry, biochemistry, molecular biology, and cheese manufacturing, are within the scope of this invention. All publications, patents, and patent applications cited herein are incorporated by reference in their entirety for all purposes.

What is claimed is:

1. A polysaccharide-protein conjugate obtained by reacting a polysaccharide comprising a reducing end and a protein in an aqueous solution comprising 10-40% (w/v) of the polysaccharide and 1-30% (w/v) of the protein, under temperature conditions of from about 40° C. to about 120° C., wherein the polysaccharide has only one reducing group per polysaccharide molecule, thereby producing a polysaccharide-protein conjugate comprising Schiff base, wherein the conjugate exhibits a maximum absorbance peak at a wavelength of less than 420 nm in difference ultraviolet spectroscopy scanned between wavelengths 270 nm and 500 nm.

2. The polysaccharide-protein conjugate of claim 1, wherein the protein comprises milk protein.

3. The polysaccharide-protein conjugate of claim 1, wherein the protein comprises hydrolyzed milk protein.

4. The polysaccharide-protein conjugate of claim 1, wherein the protein comprises protein hydrolysate.

5. The polysaccharide-protein conjugate of claim 1, wherein the polysaccharide-protein conjugate exhibits reduced allergenicity compared to the protein.

6. The polysaccharide-protein conjugate of claim 1, wherein the polysaccharide-protein conjugate is white in color for a period of at least 3 months.

7. The polysaccharide-protein conjugate of claim 1, wherein the polysaccharide-protein conjugate is thermostable for a period of at least 3 weeks in solution held at about 5° C.

8. A food composition comprising the polysaccharide-protein conjugate of claim 1.

9. A method of preparing a polysaccharide-protein conjugate as recited in claim 1, comprising reacting a polysaccharide comprising a reducing end and a protein in an aqueous solution comprising 10-40% (w/v) of the polysaccharide and 1-30% (w/v) of the protein, under temperature conditions of from about 40° C. to about 120° C., wherein the polysaccharide has only one reducing group per polysaccharide molecule, thereby producing a polysaccharide-protein conjugate comprising Schiff base, wherein the conjugate exhibits a maximum absorbance peak at a wavelength of less than 420 nm in difference ultraviolet spectroscopy scanned between wavelengths 270 nm and 500 nm.

10. The method of claim 9, wherein the protein comprises milk protein.

11. The method of claim 9, wherein the protein comprises hydrolyzed milk protein.

12. The method of claim 9, wherein the protein comprises protein hydrolysate.

13. The method of claim 9, wherein the polysaccharide-protein conjugate exhibits reduced allergenicity compared to the protein.

14. A polysaccharide-protein conjugate obtained by reacting a polysaccharide comprising a reducing end and a protein in an aqueous solution comprising 10-40% (w/v) of the polysaccharide and 1-30% (w/v) of the protein, under temperature conditions of from about 40° C. to about 120° C., wherein the polysaccharide has only one reducing group per polysaccharide molecule, thereby producing a polysaccharide-protein conjugate comprising Schiff base, wherein the polysaccharide-protein conjugate is white in color.

* * * * *